United States Patent [19]

Itoh et al.

[11] Patent Number: 4,649,219

[45] Date of Patent: Mar. 10, 1987

[54] UNSATURATED CYCLIC AMIDO-SUBSTITUTED ETHER COMPOUNDS AND PREPARATION PROCESS THEREOF

[75] Inventors: Hiroshi Itoh; Atsuhiko Nitta, both of Yokohama; Tomio Tanaka, Tokyo; Hideo Kamio, Odawara, all of Japan

[73] Assignee: Mitsui Toatsu Chemicals, Incorporated, Tokyo, Japan

[21] Appl. No.: 708,568

[22] Filed: Mar. 6, 1985

[30] Foreign Application Priority Data

Mar. 13, 1984 [JP] Japan ................................. 59-46532

[51] Int. Cl.$^4$ ............................................ C07C 103/38
[52] U.S. Cl. ................................... 564/207; 526/288; 526/292.95; 526/298; 526/304; 558/414
[58] Field of Search ............... 524/167, 171, 217, 218, 524/219, 220, 222, 224, 226; 525/279, 281, 290, 291, 296; 526/256, 257, 259, 260, 261, 263, 283, 284, 287, 288, 292.5, 304; 560/38, 39, 41; 564/153, 154, 155, 157, 204, 207

[56] References Cited

U.S. PATENT DOCUMENTS

| | | | |
|---|---|---|---|
| 2,773,063 | 12/1956 | Specht et al. | 564/208 |
| 3,037,056 | 5/1962 | Lowe et al. | 564/208 |
| 3,280,189 | 10/1966 | Cline | 564/208 |
| 3,297,623 | 1/1967 | Knapp et al. | 525/291 |
| 3,315,012 | 4/1967 | Jorgensen et al. | 525/296 |
| 3,374,289 | 3/1968 | Ott et al. | 525/296 |
| 3,433,835 | 3/1969 | Muller et al. | 564/207 |
| 3,562,327 | 2/1971 | Petersen | 560/304 |
| 3,627,831 | 12/1971 | Huber-Emden | 564/207 |
| 3,652,478 | 3/1972 | Ishii et al. | 526/304 |
| 3,705,136 | 12/1972 | Cawley et al. | 526/283 |
| 3,766,144 | 10/1973 | Hudson et al. | 525/296 |
| 3,784,565 | 1/1974 | Parker | 524/217 |
| 3,796,773 | 3/1974 | Coleman | 525/296 |
| 3,928,499 | 12/1975 | Tomalia et al. | 526/260 |
| 3,993,877 | 7/1976 | D'Alelio | 526/263 |
| 4,021,404 | 5/1977 | Cox | 524/222 |
| 4,129,545 | 12/1978 | Sunamori et al. | 526/304 |
| 4,134,916 | 1/1979 | Moss et al. | 564/207 |
| 4,172,933 | 10/1979 | Turner | 526/284 |
| 4,233,430 | 11/1980 | Jacquet et al. | 526/304 |

FOREIGN PATENT DOCUMENTS

| | | | |
|---|---|---|---|
| 204789 | 5/1955 | Australia | 564/207 |
| 312687 | 2/1956 | Fed. Rep. of Germany . | |
| 312689 | 2/1956 | Fed. Rep. of Germany . | |
| C 8498 | 8/1956 | Fed. Rep. of Germany . | |
| 1010760 | 11/1965 | United Kingdom | 564/207 |

*Primary Examiner*—Veronica P. Hoke
*Attorney, Agent, or Firm*—Fisher, Christen & Sabol

[57] ABSTRACT

Disclosed herein are novel unsaturated cyclic amide-substituted ether compounds having a wide range of utility in crosslinking agents, adhesives, paints, raw materials for hygroscopic resins, etc. These compounds are prepared by reacting cyclic halogen-substituted ether compounds with unsaturated amide compounds in the presence of a strong basic substance in an aprotic polar solvent.

4 Claims, No Drawings

UNSATURATED CYCLIC AMIDO-SUBSTITUTED ETHER COMPOUNDS AND PREPARATION PROCESS THEREOF

BACKGROUND OF THE INVENTION (a) Field of the Invention

This invention relates to unsaturated cyclic amido-substituted ether compounds and their preparation process. More specifically, it relates to unsaturated cyclic amido-substituted ether compounds, in each of which at least one hydroxyl group of an OH-substituted cyclic compound has been substituted by an unsaturated amidopolymethylenoxy group, and their preparation process. The unsaturated cyclic amido-substituted ether compounds of this invention can be used in crosslinking agents, adhesives, paints and raw materials for hygroscopic resins as well as in various other fields.

(b) Description of the Prior Art

Cyclic compounds have permitted relatively easy introduction of various substituent groups owing to their cyclic structures. This feature is not seen in aliphatic compounds, whereby making them suitable as raw materials for functional materials. When using them as functional materials, it is however necessary to increase their molecular weights, generally by fixing them to side chains of monomers so that they are insolubilized.

No general method has however been established to date for the fixing of such cyclic compounds into high molecular compounds. Except for a few examples seen among styrene derivatives, the functionality of these cyclic compounds has thus not been fully utilized under the circumstances.

As skeletal compounds of fixing base materials, N-substituted amide derivatives have some advantageous characteristics unseen in other skeletal compounds such as esters, ethers and hydrocarbon derivatives, including their better compatibility with a variety of materials, their resistance to hydrolysis, etc. compared with such other skeletal compounds.

SUMMARY OF THE INVENTION

Interested with a variety of functionality which cyclic compounds have, the present inventors have carried out an extensive investigation with a view toward fixing such cyclic compounds and developing functional polymers containing amido groups in their skeletal structures. As a result, they have found unsaturated cyclic amido-substituted ether compounds in each of which a hydroxyl group of an OH-substituted cyclic compound and the amido group of acrylic amide or methacrylic amide are bonded by way of a polymethylene group and their preparation process, leading to completion of this invention.

The unsaturated cyclic amido-substituted ether compounds can be prepared by reacting cyclic halogen-substituted ether compounds with unsaturated amide compounds in the presence of a strong basic substance in an aprotic polar solvent.

The compounds of this invention are unsaturated cyclic amido-substituted ether compounds each represented by the following general formula (I):

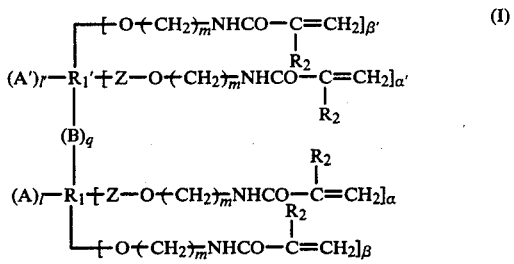

wherein $R_1$ and $R_1'$ are each a cyclic group; Z means an alkylene group having 1–5 carbon atoms, an alkenylene group having 2–5 carbon atoms, an oxyalkylene group represented by the general formula $-(O-C_xH_{2x})_r$ (r: integer of 1–50; x: integer of 1–5) or an aminoalkylene group represented by the general formula

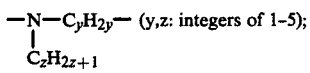

A and A' each denotes a halogen atom, hydroxyl group, oxo group, cyano group, nitro group, mercapto group, sulfo group or a salt thereof, an alkyl group having 1–20 carbon atoms, an alkenyl group having 2–15 carbon atoms, a haloalkyl group having 1–20 carbon atoms, an amino or aminoalkyl group represented by the general formula

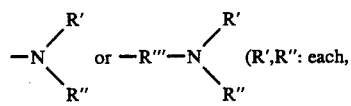

hydrogen atom, lower alkyl group or ω-unsaturated amidopolymethylene group represented by the general formula

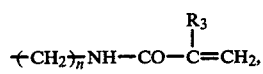

n being an integer of 4–20 and $R_3$ being a hydrogen atom or methyl group; $R'''$: lower alkylene group), a group represented by the general formula RO—, RCO— or RCOO— (R: alkyl group having 1–20 carbon atoms, alkenyl group having 2–15 carbon atoms or aryl group), a group represented by the general formula —COOR ($R_4$ hydrogen atom, alkali metal atom, alkyl group having 1–20 carbon atoms, alkenyl group having 2–15 carbon atoms, aryl group or ω-unsaturated amidopolymethylene group represented by the general formula

p being an integer of 4–20 and $R_5$ being a hydrogen atom or methyl group; B stands for an oxygen atom, carbonyl group, thio group, sulfonyl group, azo group, alkylene group having 1–5 carbon atoms or alkenylene group having 2–5 carbon atoms; $R_2$ denotes a hydrogen atom or methyl group; l and l' are each an integer of 0–5; (A)l and (A')l', each means a combination of 0–5 atoms or groups which may be the same or different and are selected from the group of the atoms and groups defined above for A and A'; m stands for an integer of 4-20; α, α', β and β' stand each for an integer of 0-4 with a proviso that all of α,α', β and β' do not stand for 0 at the same time; and q stands for 0 or 1. They are novel compounds which have not been reported in any literatures.

The compounds of this invention can each be prepared by reacting a cyclic halogen-substituted ether compound represented by the following general formula (II):

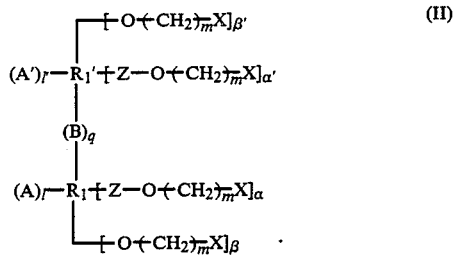

wherein $R_1$, $R_1'$, Z, A, A', B, q, m, l, l', α,α', β and β' have the same meaning as defined above and X denotes a halogen atom with an unsaturated amide compound represented by the following general formula (III):

wherein $R^2$ has the same meaning as defined above, in the presence of a strong basic substance in an aprotic polar solvent.

The cyclic halogen-substituted ether compounds which are raw materials required for the preparation of the compounds of this invention can be obtained with ease in accordance with a process already proposed by the present inventors, namely, through reactions between OH-substituted cyclic compounds and dihaloalkanes.

The following advantageous effects can thus be brought about inter alia from the practice of this invention.

(i) The process of this invention makes use of OH-substituted cyclic compounds as raw materials. Therefore, an extremely wide variety of compounds can be applied as mentioned above. The preparation process of this invention has an extremely high applicability.

Therefore, a variety of functionality may be expected on the basis of various interactions. As specific interactions, may be mentioned ionic interaction, electrostatic interaction, charge-transfer interaction, π—π interaction, van der Waals interaction and so on.

Furthermore, multi-functional monomers such as crosslinking agents can also be prepared with ease by using multi-substituted OH-substituted cyclic compounds as raw materials. New functions which are unseen in conventional crosslinking agents have been found as new types of crosslinking agents.

(ii) Since an amido group and a cyclic group are bonded together via a polymethylenoxy group and the chain length of the polymethylenoxy group can be controlled, flexibility can be imparted to polymers of the compounds of this invention and the degree of the thus-imparted flexibility can be controlled. Furthermore, the distance of bonding to an amido group can be controlled depending on the molecular size of each cyclic compound. This allows to introduce the amido group in the cyclic compound without difficulties.

(iii) An amido group is contained as a skeletal structure. Accordingly, each of the compounds of this invention has intermolecular secondary bond owing to the hydrogen bond between amido groups. Various properties have thus been improved including mechanical properties as raw materials.

DETAILED DESCRIPTION OF THE INVENTION

In the compound of this invention represented by the general formula (I), the halogen indicated by A is chlorine, bromine, iodine or fluorine. In the general formula (II), the halogen represented by X is chlorine, bromine or iodine. The carbon ring shown by $R_1$ is an aromatic or alicyclic ring or a condensed or combined ring thereof. The hetero atom which makes up the ring of the heterocyclic ring indicated by $R_1$ is oxygen, nitrogen or sulfur. Where two or more ring-forming hetero atoms are contained, they may be different from each other or one another. For example, monoheterocyclic rings, carbocyclic rings, condensed heterocyclic rings of heterocyclic rings, heterocyclic spiro rings, heterocyclic crosslinking rings, etc. may be mentioned.

As aromatic rings, may be mentioned monocyclic and condensed polycyclic rings such as benzene, naphthalene, anthracene, pentacene, heptacene and the like, and those formed of 2-4 of these rings which are bonded together. As alicyclic rings, may be mentioned monocyclic rings such as cycloalkanes, cycloalkenes, cycloalkadienes, cycloalkatrienes, etc., dimers of cycloalkadienes, hydrides of condensed aromatic polycyclic rings and those formed of 2-4 of such rings which are bonded together. As such condensed carbocyclic rings, there are dicyclic and tricyclic rings such as indene and fluorene as well as partial hydrides of condensed polycyclic aromatic compounds. Also included are hydrocarbon compounds formed of the above three types of rings combined together and those formed by substituting hetero atoms such as oxo group to ring-forming carbons.

Where A means a haloalkyl group, the above-described alkyl group contains at least one halogen atom substituted thereto. Where two or more halogen atoms are contained, they may be different halogen atoms.

The compounds of this invention are more specifically those obtained using, as basic skeletal structures, those formed of carbocyclic rings such as aromatic or alicyclic rings or their condensed or combined rings, or heterocyclic rings such as monoheterocyclic, condensed heterocyclic rings of carbocyclic rings or heterocyclic rings, heterocyclic spiro rings, crosslinked heterocyclic rings and hydroxyl groups bonded to the carbocyclic rings or heterocyclic rings either directly or via alkylene, alkenylene, oxyalkylene and/or aminoalkylene groups and substituting at least one of the hydroxyl groups with ω-unsaturated amidopolymethylenoxy group or groups. Also included are those obtained by introducing such substituent groups as referred to above with respect to A into carbocyclic rings or heterocyclic rings.

Certain representative examples of the compounds according to this invention will hereinafter be given by way of example. Since an extremely wide variety of compounds are included in the compounds of this invention, exemplary listing of compounds will first be made by changing $R_1$, $R_1'$, Z, A, A', B, l, l', α, α', β, and β' and q in various ways while setting m and $R_2$ respectively at 4 and a hydrogen atom in the general formula (1) for the sake of simplified exemplification. Then, further exemplary listing will be made by changing $R_2$ to a hydrogen atom or methyl group and m 4–20 while setting $R_1$ at a benzene ring, α, α' and β' respectively at 0, q at 0, and l' and l respectively at 0.

Among substituted derivatives of compounds which contained OH-substituted carbocyclic rings, illustrative of substituted derivatives of alicyclic monohyric alcohols include:

N-(4-Cyclobutoxybutyl)acrylic amide;
N-(4-Cyclopentyloxybutyl)acrylic amide;
N-(4-Cylohexyloxybutyl)acrylic amide;
N-[4-(1-Methylcyclopentyloxy)butyl]acrylic amide;
N-[4-(2-Cyclohexenyloxy)butyl]acrylic amide;
N-(4-Cycloheptyloxybutyl)acrylic amide;
N-[4-(Cyclohexylmethoxy)butyl]acrylic amide;
N-[4-(2-Cyclopentylethoxy)butyl]acrylic amide;
N-[4-(4-Methylcyclohexyloxy)butyl]acrylic amide;
N-[4-(2-Cyclohexylethoxy)butyl]acrylic amide;
N-(4-Cyclooctyloxybutyl)acrylic amide;
N-[4-(2,5-Dimethylcyclohexyloxy)butyl]acrylic amide;
N-[4-(3,5-Dimethylcyclohexyloxy)butyl]acrylic amide;
N-[4-(1-Ethynylcyclohexyloxy)butyl]acrylic amide;
N-[4-(2-n-Propylcyclohexyloxy)butyl]acrylic amide;
N-[4-(3,3,5-Trimethylcyclohexyloxy)butyl]acrylic amide;
N-(4-Dicyclopentadienyloxybutyl)acrylic amide;
2-(4-Acrylamidobutoxy)adamantane;
2-(4-Acrylamidobutoxy)-1,7,7-trimethylbicyclo[2.2.1]heptane;
N-[4-(5-Methyl-2-(1-methylvinyl)cyclohexyloxy)butyl]acrylic amide;
N-[4-(Dimethyl-(4-methyl-3-cyclohexenyl)methoxybutyl]acrylic amide;
N-[4-(1-Methyl-4-(1-methylvinyl)cyclohexyloxy)butyl]acrylic amide;
N-[4-(1-Methyl-4-isopropylidenecyclohexyloxy)butyl]acrylic amide;
N-[4-(4-tert-butylcyclohexyloxy)butyl]acrylic amide;
N-[4-(5-Methyl-2-isopropylcyclohexyloxy)butyl]acrylic amide;
1-(4-Actylamidobutoxymethyl)adamantane;
N-(4-Cyclododecyloxybutyl)acrylic amide;
N-[4-(2-Cyclohexylcyclohexyloxy)butyl]acrylic amide;
N-[4-(4-Cyclohexylcyclohexyloxy)butyl]acrylic amide;
3-(4-Acrylamidobutoxy)-3-cholestane;
3-(4-Acrylamidobutoxy)cholestane;
3-(4-Acrylamidobutoxy)stigmasta-5,22-diene;
3-(4-Acrylamidobutoxy)-6-stigmastene;
3-(4-Acrylamidobutoxy)lanosta-8,24-diene;
N-[4-(2-Chlorocyclohexyloxy)butyl]acrylic amide;
N-[4-(5-Oxo-2-methyl-1-cyclopentenyloxy)butyl]acrylic amide;
3-(4-Acrylamidobutoxy)-5-androsten-17-one;
17-(4-Acrylamidobutoxy)-4-androsten-3-one;
3-(4-Acrylamidobutoxy)-5-androstan-17-one;
17-(4-Acrylamidobutoxy)-5-androstan-3-one;
17-(4-Acrylamidobutoxy)-17-methyl-4-androsten-3-one;
17-(4-Acrylamidobutoxy)-17-ethynyl-4-androsten-3-one;
11-(4-Acrylamidobutoxy)progesterone;
3-(4-Acrylamidobutoxy)-5-pregnen-20-one;
21-Acetoxy-17-(4-acrylamidobutoxy)-4-pregnen-3,11,20-trione;
17-(Acrylamidobutoxy)-3-benzoyloxyestra-1,3,5(10)-triene; and the like.

As substituted derivatives of monohydric alcohols which contain aromatic rings, may for example be mentioned:

N-(4-Phenoxybutyl)acrylic amide;
N-(4-Benzyloxybutyl)acrylic amide;
N-[4-(2-Methylphenoxy)butyl]acrylic amide;
N-[4-(3-Methylphenoxy)butyl]acrylic amide;
N-[4-(4-Methylphenoxy)butyl]acrylic amide;
N-[4-(1-Phenylethoxy)butyl]acrylic amide;
N-[4-(2-Phenylethoxy)butyl]acrylic amide;
N-[4-(2,4-Dimethylphenoxy)butyl]acrylic amide;
N-[4-(3,5-Dimethylphenoxy)butyl]acrylic amide;
N-[4-(3-Ethylphenoxy)butyl]acrylic amide;
N-[4-(4-Ethylphenoxy)butyl]acrylic amide;
N-[4-(4-Methylbenzyloxy)butyl]acrylic amide;
N-[4-(1-Methyl-2-phenylethoxy)butyl]acrylic amide;
N-[4-(1-Methyl-1-phenylethoxy)butyl]acrylic amide;
N-[4-(3-Phenylpropoxy)butyl]acrylic amide;
N-[4-(4-Isopropylphenoxy)butyl]acrylic amide;
N-[4-(2-n-Propylphenoxy)butyl]acrylic amide;
N-[4-(4-n-Propylphenoxy)butyl]acrylic amide;
N-[4-(2,3,5-Trimethylphenoxy)butyl]acrylic amide;
N-[4-(3,4,5-Trimethylphenoxy)butyl]acrylic amide;
N-[4-(2-Allylphenoxy)butyl]acrylic amide;
N-[4-(1-(4-Methylphenyl)ethoxy)butyl]acrylic amide;
N-[4-(3-Phenyl-2-propenyloxy)butyl]acrylic amide;
N-[4-(1-Phenyl-2-propenyloxy)butyl]acrylic amide;
1-(4-Acrylamidobutoxy)indane;
2-(4-Acrylamidobutoxy)indane;
5-(4-Acrylamidobutoxy)indane;
N-[4-(1,1-Dimethyl-2-phenylethoxy)butyl]acrylic amide;
N-[4-(4-n-Butylphenoxy)butyl]acrylic amide;
N-[4-(2-sec-Butylphenoxy)butyl]acrylic amide;
N-[4-(4-sec-Butylphenoxy)butyl]acrylic amide;
N-[4-(2-tert-Butylphenoxy)butyl]acrylic amide;
N-[4-(3-tert-Butylphenoxy)butyl]acrylic amide;
N-[4-(4-tert-Butylphenoxy)butyl]acrylic amide;
N-[4-(1-Methyl-3-phenylpropoxy)butyl]acrylic amide;
N-[4-(2-Methyl-5-isopropylphenoxy)butyl]acrylic amide;
N-[4-(2,3,5,6-Tetramethylphenoxy)butyl]acrylic amide;
N-[4-(3-Isopropylbenzyloxy)butyl]acrylic amide;
1-(4-Acrylamidobutoxy)naphthalene;
2-(4-Acrylamidobutoxy)naphthalene;
2-(4-Acrylamidobutoxy)-5,6,7,8-tetrahydronaphthalene;
N-[4-(1,1-Dimethyl-3-phenylpropoxy)butyl]acrylic amide;
N-[4-(4-n-Pentylphenoxy)butyl]acrylic amide;
N-[4-(4-(1,1-Dimethylpropyl)phenoxy)butyl]acrylic amide;
N-[4-(2-tert-Butyl-6-methylphenoxy)butyl]acrylic amide;
N-[4-(2,6-Diisopropylphenoxy)butyl]acrylic amide;
N-[4-(6-tert-Butyl-2,4-dimethylphenoxy)butyl]acrylic amide;
N-[4-(2-Cyclohexylphenoxy)butyl]acrylic amide;
N-[4-(3-Cyclohexylphenoxy)butyl]acrylic amide;
N-[4-(4-Cyclohexylphenoxy)butyl]acrylic amide;
N-[4-(2-Phenylphenoxy)butyl]acrylic amide;
N-[4-(3-Phenylphenoxy)butyl]acrylic amide;
N-[4-(4-Phenylphenoxy)butyl]acrylic amide;
N-[4-(Diphenylmethoxy)butyl]acrylic amide;
N-[4-(4-Benzylphenoxy)butyl]acrylic amide;
N-[4-(1,1-Diphenylethoxy)butyl]acrylic amide;

N-[4-(1,2-Diphenylethoxy)butyl]acrylic amide;
N-[4-(2,4-Di-tert-butylphenoxy)butyl]acrylic amide;
N-[4-(2,6-Di-tert-butylphenoxy)butyl]acrylic amide;
N-[4-(4-(1,1,3,3-Tetramethylbutyl)phenoxy)butyl]acrylic amide;
N-[4-(4-Nonylphenoxy)butyl]acrylic amide;
N-[4-(2,6-Di-tert-butyl-4-methylphenoxy)butyl]acrylic amide;
N-[4-(4-(1-Methyl-1-phenylethyl)phenoxy)butyl]acrylic amide;
N-[4-(4-tert-butyl-2,6-diisopropylphenoxy)butyl]acrylic amide;
N-[4-(2,4,6-Tri-sec-butylphenoxy)butyl]acrylic amide;
N-[4-(2,4,6-Tri-tert-butylphenoxy)butyl]acrylic amide;
N-[4-(Triphenylmethoxy)butyl]acrylic amide; and the like.

As substituted derivatives obtained by substituting one or more halogen or haloalkyl groups to the aromatic rings of the above-described compounds, may for example be mentioned:
N-[4-(3-Fluorophenoxy)butyl]acrylic amide;
N-[4-(4-Fluorophenoxy)butyl]acrylic amide;
N-[4-(2-Chlorophenoxy)butyl]acrylic amide;
N-[4-(4-Chlorophenoxy)butyl]acrylic amide;
N-[4-(2-Bromophenoxy)butyl]acrylic amide;
N-[4-(3-Bromophenoxy)butyl]acrylic amide;
N-[4-(4-Iodophenoxy)butyl]acrylic amide;
N-[4-(2,3-Dichlorophenoxy)butyl]acrylic amide;
N-[4-(2,4-Dichlorophenoxy)butyl]acrylic amide;
N-[4-(2,6-Dichlorophenoxy)butyl]acrylic amide;
N-[4-(3,4-Dichlorophenoxy)butyl]acrylic amide;
N-[4-(3,5-Dichlorophenoxy)butyl]acrylic amide;
N-[4-(2,4-Dibromophenoxy)butyl]acrylic amide;
N-[4-(2,3,4-Trichlorophenoxy)butyl]acrylic amide;
N-[4-(2,4,5-Trichlorophenoxy)butyl]acrylic amide;
N-[4-(2,4,6-Trichlorophenoxy)butyl]acrylic amide;
N-[4-(2,4,6-Tribromophenoxy)butyl]acrylic amide;
N-[4-(2,3,4,6-Tetrachlorophenoxy)butyl]acrylic amide;
N-[4-(Pentachlorophenoxy)butyl]acrylic amide;
N-[4-(Pentabromophenoxy)butyl]acrylic amide;
N-[4-(3-Chlorobenzyloxy)butyl]acrylic amide;
N-[4-(4-Chlorobenzyloxy)butyl]acrylic amide;
N-[4-(4-Chloro-2-methylphenoxy)butyl]acrylic amide;
N-[4-(4-Chloro-3-methylphenoxy)butyl]acrylic amide;
N-[4-(2-Chloro-6-methylphenoxy)butyl]acrylic amide;
N-[4-(2-Bromo-4-methylphenoxy)butyl]acrylic amide;
N-[4-(2,4-Dichloro-6-methylphenoxy)butyl]acrylic amide;
N-[4-(2-Trifluoromethyl)phenoxy)butyl]acrylic amide;
N-[4-(2-Bromomethyl)-4,6-dibromophenoxy)butyl]acrylic amide;
N-[4-(4-Bromomethyl)-2,6-dibromophenoxy)butyl]acrylic amide;
N-[4-(Pentafluorobenzyloxy)butyl]acrylic amide;
N-[4-(4-Chloro-3,5-dimethylphenoxy)butyl]acrylic amide;
N-[4-(1-(4-Chlorophenylethoxy)butyl]acrylic amide;
N-[4-(2,4-Dichloro-3,5-dimethylphenoxy)butyl]acrylic amide;
1-(4-Acrylamidobutoxy)-4-chloronaphthalene;
N-[4-(4-tert-Butyl-2-chlorophenoxy)butyl]acrylic amide;
N-[4-(4-Chloro-5-methyl-isopropylphenoxy)butyl]acrylic amide;
2-(4-Acrylamidobutoxy)-1-bromonaphthalene;
2-(4-Acrylamidobutoxy)-6-bromonaphthalene;
N-[4-(2-Bromo-4-tert-butylphenoxy)butyl]acrylic amide;
1-(4-Acrylamidobutoxy)-2,4-dichloronaphthalene;
1-(4-Acrylamidobutoxy)-2,4-dibromonaphthalene;
N-[4-(2-Chloro-4-phenylphenoxy)butyl]acrylic amide;
N-[4-(2-Benzyl-4-chlorophenoxy)butyl]acrylic amide; etc.

As those obtained by substituting alkoxy groups to the aromatic rings of the above-described compounds and substituted derivatives obtained by bonding alkoxy groups to such aromatic rings via oxygen atoms, may for example be mentioned:
N-[4-(3-Methoxyphenoxy)butyl]acrylic amide;
N-[4-(4-Methoxyphenoxy)butyl]acrylic amide;
N-[4-(4-Methoxybenzyloxy)butyl]acrylic amide;
N-[4-(2-Methoxy-4-methylphenoxy)butyl]acrylic amide;
N-[4-(4-Ethoxyphenoxy)butyl]acrylic amide;
N-[4-(3,5-Dimethoxyphenoxy)butyl]acrylic amide;
N-[4-(2-Phenoxyethoxy)butyl]acrylic amide;
N-[4-(3,4-Dimethoxybenzyloxy)butyl]acrylic amide;
N-[4-(2-Benzyloxyethoxy)butyl]acrylic amide;
N-[4-(1-Methyl-2-phenoxyethoxy)butyl]acrylic amide;
N-[4-(2-(4-Methylphenoxy)ethoxy)butyl]acrylic amide;
N-[4-(3-n-Butoxyphenoxy)butyl]acrylic amide;
N-[4-(4-n-Butoxyphenoxy)butyl]acrylic amide;
N-[4-(4-Allyl-2-methoxyphenoxy)butyl]acrylic amide;
N-[4-(2-Methoxy-4-(1-propenyl)phenoxy)butyl]acrylic amide;
N-[4-(4-n-Pentyloxyphenoxy)butyl]acrylic amide;
N-[4-(4-n-Butoxybenzyloxy)butyl]acrylic amide;
N-[4-(2-tert-Butyl-4-methoxyphenoxy)butyl]acrylic amide;
N-[4-(4-n-Hexyloxyphenoxy)butyl]acrylic amide;
N-[4-(4-n-Heptyloxyphenoxy)butyl]acrylic amide;
N-[4-(4-n-Benzyloxyphenoxy)butyl]acrylic amide;
N-[4-(4-n-Octyloxyphenoxy)butyl]acrylic amide;
17-(4-Acrylamidobutoxy)-17-ethynyl-3-methoxy-1,3,5(10)-estratriene;
N-[4-(Phenoxy)polyethoxybutyl]acrylic amide [$CH_2=CH-CO-NH-(CH_2)_4 O-(CH_2CH_2-O)_n C_6H_5$; n=5, 7.5, 10, 15, 18, 20];
N-[4-((4-Nonylphenoxy)polyethoxy)butyl]acrylic amide [$CH_2=CH-CO-NH-(CH_2-)_4O-(CH_2CH_2-O)_n C_6H_5-C_9H_{19}$; n=5, 7.5, 10, 15, 18, 20 ];
N-[4-(2-(4-Chlorophenoxy)ethoxy)butyl]acrylic amide; and etc.

As those obtained by substituting cyano, nitro, amino and/or aminoalkyl groups to the aromatic rings of the above-described compounds or substituted derivatives formed by bonding such groups to the aromatic rings via azo groups, may for example be mentioned:
N-[4-(4-Cyanophenoxy)butyl]acrylic amide;
N-[4-(2-Nitrophenoxy)butyl]acrylic amide;
N-[4-(3-Nitrophenoxy)butyl]acrylic amide;
N-[4-(4-Nitrophenoxy)butyl]acrylic amide;
N-[4-(2-Chloro-4-nitrophenoxy)butyl]acrylic amide;
N-[4-(4-Chloro-2-nitrophenoxy)butyl]acrylic amide;
N-[4-(2,6-Dichloro-4-nitrophenoxy)butyl]acrylic amide;
N-[4-(2,4-Dinitrophenoxy)butyl]acrylic amide;
N-[4-(2,5-Dinitrophenoxy)butyl]acrylic amide;
N-[4-(4-Methyl-3-nitrophenoxy)butyl]acrylic amide;
N-[4-(2-Methyl-4-nitrophenoxy)butyl]acrylic amide;
N-[4-(3-Nitrobenzyloxy)butyl]acrylic amide;
N-[4-(4-Nitrobenzyloxy)butyl]acrylic amide;
N-[4-(4-Nitro-3-trifluoromethylphenoxy)butyl]acrylic amide;
N-[4-(3,5-Dinitro-2-methylphenoxy)butyl]acrylic amide;

N-[4-(2-Methoxy-5-nitrophenoxy)butyl]acrylic amide;
N-[4-(2-Anilinoethoxy)butyl]acrylic amide;
α-(4-Acrylamidobutoxy)benzyl cyanamide;
N-[4-(5-Dimethylamino-2-nitrophenoxy)butyl]acrylic amide;
N-[4-(3-(Dimethylamino)phenoxy)butyl]acrylic amide;
N-[4-(Dimethylaminomethylphenoxy)butyl]acrylic amide;
N-[4-(2-Amino-1-phenylpropoxy)butyl]acrylic amide;
N-[4-(2-(2-Methylphenylamino)ethoxy)butyl]acrylic amide;
2-(4-Acrylamidobutoxy)-1-nitronaphthalene;
1-(4-Acrylamidobutoxy)-2,4-dinitronaphthalene;
N-[4-(2-(N-ethylanilino)ethoxy)butyl]acrylic amide;
N-[4-(3-(diethylamino)phenoxy)butyl]acrylic amide;
N-[2-(4-Acrylamidobutoxy)ethyl]phthalimide;
N-[4-(1-(3-(Dimethylamino)phenyl)ethoxy)butyl]acrylic amide;
N-[4-(4-(2-(Dimethylamino)ethyl)phenoxy)butyl]acrylic amide;
N-[4-(2-(N-(2-Cyanoethyl)anilino)ethoxy)butyl]acrylic amide;
N-[4-(2-(N-ethyl-m-toluidino)ethoxy)butyl]acrylic amide;
N-[4-(4-Phenylazophenoxy)butyl]acrylic amide;
N-[4-(2-(N-(2-Cyanoethyl)-m-toluidino)ethoxy)butyl]acrylic amide;
N-[4-(4-(Phenylamino)phenoxy)butyl]acrylic amide;
N-[4-(4-(4-Cyanophenyl)phenoxy)butyl]acrylic amide;
N-[4-(2-(Phenyliminomethyl)phenoxy)butyl]acrylic amide;
N-[4-(4-Benzylaminophenoxy)butyl]acrylic amide;
N-[4-(4-Methyl-2-phenylazophenoxy)butyl]acrylic amide;
N-[4-(2,4,6-Tris(dimethylaminomethyl)phenoxy)butyl]acrylic amide;
N-[4-(2-(Dibenzylamino)ethoxy)butyl]acrylic amide;
2-(4-Acrylamidobutoxy)-1-phenylazonaphthalene;
1-(4-Acrylamidobutoxy)-4-(4-nitrophenyl)azonaphthalene;
2-(4-Acrylamidobutoxy)-(2-methylphenyl)azonaphthalene;
2-(4-Acrylamidobutoxy)-1-(2,5-dimethylphenyl)azonaphthalene;
N-[4-(2-(4-Acrylamidobutylamino)phenoxy)butyl]acrylic amide;
N-[4-(2-(4-Acrylamidobutylamino)-4-chlorophenoxy)butyl]acrylic amide;
N-[4-(4-(4-Acrylamidobutylamino)-2,6-dichlorophenoxy)butyl]acrylic amide;
N-[4-(2-(4-Acrylamidobutylamino)-4-nitrophenoxy)butyl]acrylic amide;
N-[4-(4-(4-Acrylamidobutylamino)-2-nitrophenoxy)butyl]acrylic amide;
N-[4-(2,4-Bis(4-acrylamidobutylamino)phenoxy)butyl]acrylic amide;
N-[4-(2-(4-Acrylamidobutylamino)-4,6-dinitrophenoxy)butyl]acrylic amide;
N-[4-(2-(4-Acrylamidobutylamino)-4-methylphenoxy)butyl]acrylic amide;
N-[4-(2-(4-(4-Acrylamidobutylamino)phenyl)ethoxy)butyl]acrylic amide;
3-(4-Acrylamidobutoxy)-2-(4-acrylamidobutylamino)anthraquinone;
1-(4-Acrylamidobutoxy)-4-(4-acrylamidobutylamino)naphthalene;
2-(4-Acrylamidobutoxy)-8-(4-acrylamidobutylamino)naphthalene;
4-(4-Acrylamidobutylamino)-N-[2-(4-acrylamidobutoxy)ethyl]-N-ethylaniline;
N-[4-(2-(4-Acrylamidobutylamino)-4-phenylphenoxy)butyl]acrylic amide; etc.

As those obtained by substituting aldehydo, acyl, acyloxy, carboxyl and/or esterified carboxyl groups to the aromatic rings of the above-described compounds and substituted derivatives formed by bonding such groups to the aromatic rings via carbonyl groups, may for example be mentioned:
N-[4-(2-Formylphenoxy)butyl]acrylic amide;
N-[4-(3-Formylphenoxy)butyl]acrylic amide;
N-[4-(4-Formylphenoxy)butyl]acrylic amide;
1-(4-Acrylamidobutoxy)cyclohepta-1,3,5-triene-7-one;
N-[4-(Benzoylmethoxy)butyl]acrylic amide;
N-[4-(2-Acetylphenoxy)butyl]acrylic amide;
N-[4-(3-Acetylphenoxy)butyl]acrylic amide;
N-[4-(4-Acetylphenoxy)butyl]acrylic amide;
N-[4-(4-Formyl-2-methoxyphenoxy)butyl]acrylic amide;
N-[4-(5-Acetyl-2-methoxyphenoxy)butyl]acrylic amide;
N-[4-(2-Acetyl-6-methoxyphenoxy)butyl]acrylic amide;
N-[4-(2-Propionylphenoxy)butyl]acrylic amide;
N-[4-(4-Propionylphenoxy)butyl]acrylic amide;
N-[4-(2-Ethoxy-6-formylphenoxy)butyl]acrylic amide;
N-[4-(2-Ethoxy-4-formylphenoxy)butyl]acrylic amide;
N-[4-(4-Formyl-2,6-dimethoxyphenoxy)butyl]acrylic amide;
N-[4-(4-Acetyl-2-methoxyphenoxy)butyl]acrylic amide;
2-(4-Acrylamidobutoxy)-1,4-naphthoquinone;
5-(4-Acrylamidobutoxy)-1,4-naphthoquinone;
1-(4-Acrylamidobutoxy)-2-isopropylcyclohepta-1,3,5-trien-7-one;
2-(4-Acrylamidobutoxy)-9-fluorene;
2-(4-Acrylamidobutoxy)benzophenone;
4-(4-Acrylamidobutoxy)benzophenone;
2-(4-Acrylamidobutoxy)-2-phenylacetophenone;
2-(4-Acrylamidobutoxy)anthoraquinone;
2-(4-Acrylamidobutoxy)-4-methoxybenzophenone;
2-(4-Acrylamidobutoxy)benzalacetophenone;
2'-(4-Acrylamidobutoxy)benzalacetophenone; 3-(4-Acrylamidobutoxy)estra-1,3,5(10)-trien-17-one;
2-(4-Acrylamidobutoxy)-4-n-octyloxybenzophenone;
N-[4-(4-chloro-2-formylphenoxy)butyl]acrylic amide;
N-[4-(4-Bromo-2-formylphenoxy)butyl]acrylic amide;
N-[4-(2,4-Dichloro-6-formylphenoxy)butyl]acrylic amide;
N-[4-(2,4-Dibromo-6-formylphenoxy)butyl]acrylic amide;
N-[4-(2-Formyl-4-nitrophenoxy)butyl]acrylic amide;
N-[4-(4-Bromo-1-formyl-6-nitrophenoxy)butyl]acrylic amide;
4-Acrylamidobutyl 2-(4-arylamidobutoxy)benzoate;
Methyl 2-(4-acrylamidobutoxy)benzoate;
Ethyl 2-(4-acrylamidobutoxy)benzoate;
Isopropyl 2-(4-acrylamidobutoxy)benzoate;
n-Butyl 2-(4-acrylamidobutoxy)benzoate;
3-Methylbutyl 2-(4-acrylamidobutoxy)benzoate;
3-Hexenyl 2-(4-acrylamidobutoxy)benzoate;
Phenyl 2-(4-acrylamidobutoxy)benzoate;
4-Methylphenyl 2-(4-acrylamidobutoxy)benzoate;
Benzyl 2-(4-acrylamidobutoxy)benzoate;
4-tert-Butylphenyl 2-(4-acrylamidobutoxy)benzoate;
4-Octylphenyl 2-(4-acrylamidobutoxy)benzoate;
4-Nitrophenyl 2-(4-acrylamidobutoxy)benzoate;

4-Acrylamidobutyl 3-(4-acrylamidobutoxy)benzoate;
Methyl 3-(4-acrylamidobutoxy)benzoate;
Ethyl 3-(4-acrylamidobutoxy)benzoate;
4-Acrylamidobutyl 4-(4-acrylamidobutoxy)benzoate;
Methyl 4-(4-acrylamidobutoxy)benzoate;
Ethyl 4-(4-acrylamidobutoxy)benzoate;
n-Propyl 4-(4-acrylamidobutoxy)benzoate;
n-Butyl 4-(4-acrylamidobutoxy)benzoate;
n-Pentyl 4-(4-acrylamidobutoxy)benzoate;
3-Methylbutyl 4-(4-acrylamidobutoxy)benzoate;
n-Hexyl 4-(4-acrylamidobutoxy)benzoate;
n-Heptyl 4-(4-acrylamidobutoxy)benzoate;
2-Ethylhexyl 4-(4-acrylamidobutoxy)benzoate;
n-Nonyl 4-(4-acrylamidobutoxy)benzoate;
n-Dodecyl 4-(4-acrylamidobutoxy)benzoate;
Phenyl 4-(4-acrylamidobutoxy)benzoate;
Benzyl 4-(4-acrylamidobutoxy)benzoate;
4-Acrylamidobutyl 2-(4-acrylamidobutoxy)phenylacetate;
4-Acrylamidobutyl 3-(4-acrylamidobutoxy)phenylacetate;
4-Acrylamidobutyl 4-(4-acrylamidobutoxy)phenylacetate;
4-Acrylamidobutyl α-(4-acrylamidobutoxy)phenylacetate;
Methyl α-(4-acrylamidobutoxy)phenylacetate;
Ethyl α-(4-acrylamidobutoxy)phenylacetate;
3-Methylbutyl α-(4-acrylamidobutoxy)phenylacetate;
Benzyl α-(4-acrylamidobutoxy)phenylacetate;
4-Acrylamidobutyl 2-(4-acrylamidobutoxy)-3-methylbenzoate;
4-Acrylamidobutyl 2-(4-acrylamidobutoxy)-4-methylbenzoate;
4-Acrylamidobutyl 2-(4-acrylamidobutoxy)-5-methylbenzoate;
N-[4-(3-Acetyloxyphenoxy)butyl]acrylic amide;
4-Acrylamidobutyl 4-(4-actylamidobutoxy)-3-methoxybenzoate;
4-Acrylamidobutyl 3-(4-actylamidobutoxy)-4-methoxybenzoate;
4-Acrylamidobutyl 3-[2-(4-acrylamidobutoxy)phenyl]-2-propenate;
4-Acrylamidobutyl 3-[3-(4-acrylamidobutoxy)phenyl]-2-propenate;
4-Acrylamidobutyl 3-[4-(4-acrylamidobutoxy)phenyl]-2-propenate;
4-Acrylamidobutyl α-(4-acrylamidobutoxymethyl)phenylacetate;
4-Acrylamidobutyl 4-(4-acrylamidobutoxy)-3-methoxyphenylacetate;
4-Acrylamidobutyl 4-(4-acrylamidobutoxy)-3,5-dimethoxybenzoate;
4-Acrylamidobutyl 3-(4-acrylamidobutoxy)-4-methoxycinnamate;
4-Acrylamidobutyl 4-(4-acrylamidobutoxy)-3-methoxycinnamate;
4-Acrylamidobutyl 4-(4-acrylamidobutoxy)-3-methoxyphenylpyruvate;
4-Acrylamidobutyl 1-(4-acrylamidobutoxy)-2-naphthoate;
4-Acrylamidobutyl 2-(4-acrylamidobutoxy)-3-naphthoate;
Methyl 2-(4-acrylamidobutoxy)-3-naphthoate;
4-Acrylamidobutyl 2-(4-acrylamidobutoxy)-1-naphthoate;
4-Acrylamidobutyl 2-(4-acrylamidobutoxy)-3-phenylbenzoate;
N-[4-(3-Benzoyloxyphenoxy)butyl]acrylic amide;
4-Acrylamidobutyl α-(4-acrylamidobutoxy)-α-phenylphenylacetate;
Stearyl β-[4-(4-acrylamidobutoxy)-3,5-di-tertbutylphenyl]propionate;
4-Acrylamidobutyl 2-(4-acrylamidobutoxy)-5-chlorobenzoate;
4-Acrylamidobutyl 2-(4-acrylamidobutoxy)-3,5-dichlorobenzoate;
4-Acrylamidobutyl 4-(4-acrylamidobutoxy)-3,5-dichlorobenzoate;
Ethyl 4-(4-acrylamidobutoxy)-3,5-dichlorobenzoate;
4-Acrylamidobutyl 2-(4-acrylamidobutoxy)-5-bromobenzoate;
4-Acrylamidobutyl 2-(4-acrylamidobutoxy)-3,5-dibromobenzoate;
4-Bromophenyl 2-(4-acrylamidobutoxy)-3,5-dibromobenzoate;
4-Acrylamidobutyl α-(4-acrylamidobutoxy)-4-chlorophenylbenzoate;
4-Acrylamidobutyl α-(4-acrylamidobutoxy)-4-bromophenylbenzoate;
4-Acrylamidobutyl 2-(4-acrylamidobutoxy)-3-nitrobenzoate;
4-Acrylamidobutyl 2-(4-acrylamidobutoxy)-3,5-dinitrobenzoate;
4-Acrylamidobutyl 2-(4-acrylamidobutoxy)-5-nitrophenyl)azobenzoate;
4-Acrylamidobutyl 2-(4-acrylamidobutoxy)-4-(4-acrylamidobutylamino)benzoate; etc.

As those formed by substituting mercapto groups or sulfo groups or their salts to the aromatic rings of the above-described compounds and substituted derivatives obtained by bonding such groups to the aromatic rings via thio groups, may for example be mentioned:
Sodium 4-(4-(acrylamidobutoxy)benzenesulfonate;
N-[4-(4-(methylthio)phenoxy)butyl]acrylic amide;
Sodium 1-(4-acrylamidobutoxy)-2-methyl-4-benzenesulfonate;
Sodium 1-(4-acrylamidobutoxy)-2-methoxybenzenesulfonate;
Disodium 2-(4-acrylamidobutoxy)-5-sulfobenzoate;
N-[4-(2-(phenylthio)ethoxy)butyl]acrylic amide;
N-[4-(3-methyl-4-(methylthio)phenoxy)butyl]acrylic amide;
Sodium 1-(4-acrylamidobutoxy)-2-naphthalenesulfonate;
Sodium 1-(4-acrylamidobutoxy)-3-naphthalenesulfonate;
Sodium 1-(4-acrylamidobutoxy)-5-naphthalenesulfonate;
Sodium 1-(4-acrylamidobutoxy)-3,6-naphthalenedisulfonate;
Disodium 2-(4-acrylamidobutoxy)-6,8-naphthalenedisulfonate;
Sodium 4-[4-(4-acrylamidobutoxy)phenylazo]-benzenesulfonate;
Sodium 4-[4-(4-acrylamidobutoxy)-1-naphthyl)azo]benzenesulfonate;
Disodium 2-(4-acrylamidobutoxy)-1-(p-sulfophenylazo)-6-naphthalenesulfonate;
Trisodium 2-(4-acrylamidobutoxy)-1-(4-sulfo-1-naphthylazo)-3,6-naphthalenesulfonate;
Trisodium 1-(4-sulfo-1-naphthylazo)-2-naphthol-6,8-disulfonate;
Sodium 2-(4-acrylamidobutoxy)-1-(4-acrylamidobutylamino)-5-nitro-3-benzenesulfonate;
Sodium 2-(4-acrylamidobutoxy)-1-(4-acrylamidobutylamino)-5-chloro-3-benzenesulfonate;
Sodium 2-(4-acrylamidobutoxy)-1-(4-acrylamidobutylamino)-4-naphthalenesulfonate; etc.

Among substituted derivatives of compounds which contain OH-substituted carbocyclic rings, exemplary substituted derivatives of aliphatic polyhydric alcohols may include:

N-[4-(2-Hydroxycyclohexyloxy)butyl]acrylic amide;
1,4-Bis[4-acrylamidobutoxy)cyclohexane;
N-[4-(3-Hydroxy-2,2,4,4-tetramethylcyclobutoxy)-butyl]acrylic amide;
2-[4-(4-Acrylamidobutoxy)cyclohexyl]-2-(4-hydroxycyclohexyl)propane;
2,2-Bis[4-(4-Acrylamidobutoxy)cyclohexyl]propane;
1,4-Bis(4-acrylamidobutoxymethyl)cyclohexane;
N-4[-(1,3-Dimethyl-7-hydroxy-5-adamantyloxy)butyl]acrylic amide;
5,7-Bis(4-acrylamidobutoxy)-1,3-dimethyladamantane;
N-[4-(2-Hydroxycyclododecyloxy)butyl]acrylic amide;
1,2-Bis(4-acrylamidobutoxy)cyclododecane;
1,2-(Bis(4-acrylamidobutoxy)-5,9-cyclododecadiene;
3-(4-Acrylamidobutoxy)-17-methyl-5-androsten-17-ol;
3,17-Bis(4-acrylamidobutoxy)-17-methyl-5-androstane;
3-(4-Acrylamidobutoxy)-5-Pregnan-20-ol;
3,20-Bis(4-acrylamidobutoxy)-5-pregnane;
3-(4-Acrylamidobutoxy)-17-ethynyl-1,3,5(10)-estratrien-17-ol;
3,20-Bis(4-acrylamidobutoxy)-17-ethynyl-5(10)-estratriene;
3-(4-Acrylamidobutoxy)-estra-1,3,5(10)-trien-17ol;
3,17-Bis(4-acrylamidobutoxy)-estra-1,3,5(10)-triene;
3-(4-Acrylamidobutoxy)-estra-1,3,5(10)-trien6,17-diol;
3,16-Bis(4-acrylamidobutoxy)-estra-1,3,5(10)-trien-17-ol;
3,16,17-Tris(4-acrylamidobutoxy)-estra-1,3,5(10)-triene;
3-(4-Acrylamidobutoxy)-4-hydroxy-3-cyclobuten-1,2-dione;
3,4-Bis(4-acrylamidobutoxy)-3-cyclobuten-1,2-dione;
11,17-Bis(4-acrylamidobutoxy)-17-methyl-4-androstroen-3-one;
21-(4-Acrylamidobutoxy)-11-hydroxy-4-pregnen-3,20-dione;
11,21-Bis(4-acrylamidobutoxy)-4-pregnen-3,20-dione;
3,17-Bis(4-acrylamidobutoxy)-5-pregnen-20-one;
3,14-Bis(4-acrylamidobutoxy)-5-cardo-20(22)-enolide;
11-(4-Acrylamidobutoxy)-17,21-dihydroxy-1,4-pregnadien-3,20-dione;
11,21-Bis(4-acrylamidobutoxy)-17-hydroxy-1,4-pregnadien-3,20-dione;
11,17,21-Tris(4-acrylamidobutoxy)-4-pregnen-3,20-dione;
21-Acetoxy-11,17-bis(4-acrylamidobutoxy)-4-pregnen-3,20-dione;
Sodium 3-(4-acrylamidobutoxy)-12-hydroxy-5-cholanate;
Sodium 3,6-bis(4-acrylamidobutoxy)-5-cholanate;
Sodium bis(4-acrylamidobutoxy)hydroxy-1-cyclohexenecarboxylate; etc.

Among substituted derivatives of compounds containing OH-substituted carbocyclic rings, illustrative of substituted derivatives of polyhydric alcohols of compounds, which contain aromatic rings, may include:

N-[4-(2-Hydroxyphenoxy)butyl]acrylic amide;
1,2-Bis(4-acrylamidobutoxy)benzene;
N-[4-(3-Hydroxyphenoxy)butyl]acrylic amide;
1,3-Bis(4-acrylamidobutoxy)benzene;
N-[4-(4-Hydroxyphenoxy)butyl]acrylic amide;
1,4-Bis(4-acrylamidobutoxy)benzene;
N-[4-(4-Hydroxyphenylmethoxy)butyl]acrylic amide;
N-[4-(4-(Hydroxymethyl)phenoxy)butyl]acrylic amide;
N-[4-(4-(4-acrylamidobutoxy)phenylmethoxy)butyl]acrylic amide;
2,3-Bis(4-acrylamidobutoxy)toluene;
N-[4-(2-Hydroxy-5-methylphenoxy)butyl]acrylic amide;
3,5-Bis[4-acrylamidobutoxy)toluene;
N-[4-(4-Hydroxy-2-methylphenoxy)butyl]acrylic amide;
N-[4-(4-Ethyl-3-hydroxyphenoxy)butyl]acrylic amide;
2,4-Bis(4-acrylamidobutoxy)-1-ethylbenzene;
N-[4-(4-(Hydroxymethyl)benzyloxy)butyl]acrylic amide;
1,4-Bis(4-acrylamidobutoxymethyl)benzene;
N-[4-(4-Hydroxy-2,3,6-trimethylphenoxy)butyl]acrylic amide;
1,4-Bis(4-acrylamidobutoxy)-trimethylbenzene;
3-(4-Acrylamidobutoxy)-1-naphthol;
1,4-Bis(4-acrylamidobutoxy)naphthalene;
N-[4-(5-tert-Butyl-2-hydroxyphenoxy)butyl]acrylic amide;
1,2-Bis(4-acrylamidobutoxy)-4-tert-butylbenzene;
N-[4-(2-Hydroxy-2-phenylethoxy)butyl]acrylic amide;
[1,2-Bis(4-acrylamidobutoxy)ethyl]benzene;
N-[4-(3-Hydroxy-2-methyl-2-phenylpropoxy)butyl]acrylic amide;
[1,1-Bis(4-acrylamidobutoxymethyl)ethyl]benzene;
N-[4-(4-Hydroxy-tetramethylphenoxy)butyl]acrylic amide;

(4-acrylamidobutoxy)durene; Bis
N-[4-(2-(2-Hydroxyphenyl)phenoxy)butyl]acrylic amide;
2,2'-Bis(4-acrylamidobutoxy)diphenyl;
N-[4-(2-(n-Hexyl)-5-hydroxyphenoxy)butyl]acrylic amide;
Bis(4-acrylamidobutoxymethyl)durene;
2,4-Bis(4-acrylamidobutoxy)-1-(n-hexyl)benzene;
N-[4-(4-Benzyl-3-hydroxyphenoxy)butyl]acrylic amide;
1-Benzyl-2,4-bis[acrylamidobutoxy)benzene;
N-[4-(4-(4-Hydroxybenzyl)phenoxy)butyl]acrylic amide;
Bis[4-(4-acrylamidobutoxy)phenyl]methane;
N-[4-(2,4-Di-tert-butyl-6-hydroxyphenoxy)butyl]acrylic amide;
1,4-Bis(4-acrylamidobutoxy)-2,5-di-tert-butylbenzene;
N-[4-(5-Hydroxy-2-(1,1,3,3)-tetramethylbutyl)phenoxy)butyl]acrylic amide;
2,4-Bis(4-acrylamidobutoxy)-1-(1,1,3,3-tetramethylbutyl)benzene;
2-[4-(4-Acrylamidobutoxy)phenyl]-2-(4-hydroxyphenyl)propane;
2,2-Bis[4-(4-acrylamidobutoxy)phenyl]propane;
N-[4-(4-Hydroxy-3,5-di-tert-butylbenzyloxy)butyl]acrylic amide;
N-[4-(4-(4-Acrylamidobutoxy)-3,5-di-tert-butylbenzyloxy)butyl]acrylic amide;
2-[4-(4-Acrylamidobutoxy)phenyl]-2-(4-hydroxyphenyl)butane;
2,2-Bis[4-(4-acrylamidobutoxy)phenyl]butane;
N-[4-(2,5-Bis(1,1-dimethylpropyl)-4-hydroxyphenoxy)butyl]acrylic amide;
1,4-Bis(4-acrylamidobutoxy)-2,5-bis(1,1-imethylpropyl)benzene;
3-[4-(4-Acrylamidobutoxy)phenyl]-4-(4-hydroxyphenyl)-2,4-hexadiene;
3,4-Bis[4-(4-acrylamidobutoxy)phenyl]-2,4-hexadiene;
3-[4-(4-Acrylamidobutoxy)phenyl]-4-(4-hydroxy phenyl)-3-hexene;

3,4-Bis[4-(4-acrylamidobutoxy)phenyl]-3-hexene;
3-[4-(4-Acrylamidobutoxy)phenyl]-4-(4-hydroxyphenyl)-n-hexane;
3,4-Bis[4-(4-acrylamidobutoxy)phenyl]-n-hexane;
2-(4-acrylamidobutoxy)-2'-hydroxy-1,1'-dinaphthyl;
2,2'-Bis(4-acrylamidobutoxy)-1,1'-dinaphthyl;
2-[2-(4-Acrylamidobutoxy)-3-tert-butyl-5-methylbenzyl]6-tert-butyl-p-cresol;
3,3'-Methylenebis[4-(4-acrylamidobutoxy)-5-tert-butyltoluene];
2-[2-(4-Acrylamidobutoxy)-3-tert-butyl-5-ethylbenzyl]-6-tert-butyl-4-ethylphenol;
1,1'-Methylenebis[2-(4-acrylamidobutoxy)-3-tert-butyl-5-ethylbenzene];
N-[4-(2-Hydroxy-tetraphenylethoxy)butyl]acrylic amide;
1,2-Bis(4-acrylamidobutoxy)-tetraphenylethane;
1-[4-(4-Acrylamidobutoxy)-5-tert-butyl-3-methylphenyl]-1-(5-tert-butyl-4-hydroxy-2-methylphenyl)-n-butane;
2,2'-Butylidenebis[5-(4-acrylamidobutoxy)-4-tert-butyltoluene];
N-[4-(4-(3,5-Di-tert-butyl-4-hydroxybenzyl)-2,6-di-tert-butylphenoxy)butyl]acrylic amide;
1,1'-Methylenebis[4-(4-acrylamidobutoxy)-3,5-di-tert-butylbenzene];
2-(4-Acrylamidobutoxy)resorcin;
2,3-Bis(4-acrylamidobutoxy)phenol;
2,6-Bis(4-acrylamidobutoxy)phenol;
1,2,3-Tris(4-acrylamidobutoxy)benzene;
5-(4-Acrylamidobutoxy)resorcin;
1,3,5-Tris(4-acrylamidobutoxy)benzene;
4-(4-Acrylamidobutoxy)catechol;
2-(4-Acrylamidobutoxy)hydroquinone;
1-(4-Acrylamidobutoxymethyl)-2-[bis(4-hydroxyphenyl)methyl]benzene;
2-[(4-(4-Acrylamidobutoxy)phenyl)-(4-hydroxyphenyl)methyl]benzyl alcohol;
4-[(2-(4-Acrylamidobutoxymethyl)phenyl)-(4-(4-acrylamidobutoxy)phenyl)methyl]phenol;
2-[Bis(4-(4-acrylamidobutoxy)phenyl)methyl]benzyl alcohol;
1-(4-Acrylamidobutoxymethyl)-2-[bis(4-(4-bromobutoxy)phenyl)methyl]benzene;
3-[4-(4-Acrylamidobutoxy)-5-tert-butyl-2-methylphenyl]-1,1-bis(5-tert-butyl-4-hydroxy-2-methylphenyl)butane;
1,1,3-Tris[4-(4-acrylamidobutoxy)-5-tert-butyl-2-methylphenyl]butane;
1,3-Bis[4-[4-acrylamidobutoxy)-3,5-di-tertbutylbenzyl]-5-(3,5-di-tert-butyl-4-hydroxybenzyl)-2,4,6-trimethylbenzene;
1,3,5-Trimethyl-2,4,6-tris[4-(4-acrylamidobutoxy)-3,5-di-tert-butylbenzyl]benzene;
1-(4-Acrylamidobutoxy)-4,9,10-trihydroxyantracene;
1,4-Bis(4-acrylamidobutoxy)-9,10-dihydroxyanthracene;
1,4,9-Tris(4-acrylamidobutoxy)-10-hydroxyanthracene;
1,4,9,10-Tetrakis(4-acrylamidobutoxy)anthracene; etc.

As derivatives obtained by substituting halogen atoms and/or haloalkyl groups to the aromatic rings of the above-described compounds, may for example be mentioned:
1,4-Bis(4-acrylamidobutoxy)tetrachlorobenzene;
1,1'-Methylenebis[2-(4-acrylamidobutoxy)-5-chlorobenzene];
2,2-Bis[4-(4-acrylamidobutoxy)-3,5-dichlorophenyl]propane; 2,2-Bis[4-(4-acrylamidobutoxy)-3,5-dibromophenyl]propane;
2,2-Bis[4-(2-(4-acrylamidobutoxy)ethoxy-3,5-dibromophenyl]propane;
1,2-Bis(4-acrylamidobutoxy)-4-chlorobenzene;
1,3-Bis(4-acrylamidobutoxy)-4-bromobenzene;
1,5-Bis(4-acrylamidobutoxy)-2,4-dichlorobenzene;
1,3-Bis(4-acrylamidobutoxy)tetrafluorobenzene; etc.

As substituted derivatives of those obtained by substituting alkoxy groups to aromatic rings of the above-described compounds and those formed by bonding such alkoxy groups to the aromatic rings via oxygen atoms, may for example be mentioned:
N-[4-(2-Hydroxy-3-methoxyphenoxy)butyl]acrylic amide;
1,2-Bis(4-acrylamidobutoxy)-3-methoxybenzene;
N-[4-(4-Hydroxy-3-methoxyphenoxy)butyl]acrylic amide;
N-[4-(4-(hydroxymethyl)-2-methoxyphenoxy)butyl]acrylic amide;
1-(4-Acrylamidobutoxy)-4-(4-acrylamidobutoxymethyl)-2-methoxybenzene;
N-[4-(2-(4-(2-Hydroxyethoxy)phenoxy)butyl]acrylic amide;
1,4-Bis[2-(4-acrylamidobutoxy)ethoxy]benzene;
1-(4-Acrylamidobutoxy)-3-(2-methoxyphenoxy)-2-propanol;
1,2-Bis(4-acrylamidobutoxy)-3-(2-methoxyphenoxy)-propane; etc.

As substituted derivatives of those obtained by substituting cyano, nitro, amino and/or alkylamino groups to aromatic rings of the above-described compounds and those formed by bonding such groups to the aromatic rings via azo groups, may for example be mentioned:
2-(4-Acrylamidobutoxy)-4-nitrophenol;
1,2-Bis(4-acrylamidobutoxy)-4-nitrobenzene;
2,4-Bis(4-acrylamidobutoxy)-1-nitrobenzene;
1,3-Bis(4-acrylamidobutoxy)-2,4-dinitrobenzene;
2,4-Bis(4-acrylamidobutoxy)-1,3,5-trinitrobenzene;
4-(4-Acrylamidobutoxy)mandelonitrile;
4-[(4-Acrylamidobutoxy)cyanomethyl]phenol;
1-(4-Acrylamidobutoxy)-4-[(4-acrylamidobutoxy)-cyanomethyl]benzene;
1-(4-Acrylamidobutoxy)-3-[1-(4-acrylamidobutoxy)-2-methylaminoethyl]benzene;
2-(4-Acrylamidobutoxy)-5-[1-(4-acrylamidobutoxy)-2-methylaminoethyl]phenol;
4-[1-(4-Acrylamidobutoxy)-2-methylaminoethyl]-1,2-bis(4-acrylamidobutoxy)benzene;
N-[2-(4-Acrylamidobutoxy)ethyl]-N-(2-hydroxyethyl)aniline;
N,N-Bis[2-(4-acrylamidobutoxy)ethyl]aniline;
N,N-Bis[2-(4-acrylamidobutoxy)ethyl]-3-chloroaniline;
N,N-Bis[2-(4-acrylamidobutoxy)ethyl]-3-methylaniline;
N-[2-(4-Acrylamidobutoxy)ethyl]-N-(2-hydroxyethyl)-4-methylaniline;
N-[2-(4-Acrylamidobutoxy)propyl]-N-(2-hydroxypropyl)aniline;
4-[1-(4-Acrylamidobutoxy)-2-isopropylaminoethyl]-1,2-bis(4-acrylamidobutoxy)benzene;
1,2-Bis(4-acrylamidobutoxy)-4-(4-nitrophenyl)azobenzene;
1,3-Bis(4-acrylamidobutoxy)-4-(4-nitrophenyl)azobenzene;
1,1'-Azobis[2-(4-acrylamidobutoxy)benzen],
1,3-Bis[4-acrylamidobutoxy)-4-phenylazobenzene;
3,3'-Bis(4-acrylamidobutoxy)diphenylamine;

3,5-Bis(4-acrylamidobutoxy)-4-(4-nitrophenyl)azotoluene;
1,3-Bis(4-acrylamidobutoxy)-2-(fluorene-2-azo)benzene;
1,1'-Bis[4-(4-(4-acrylamidobutoxy)phenylazo)-3-nitrobenzene]; etc.

As substituted derivatives of those obtained by substituting aldehydo, acyl, acyloxy, carboxyl, and/or esterified carboxyl groups to aromatic rings of the above-described compounds and those formed by bonding such groups to the aromatic rings via carbonyl groups, may for example be mentioned:

2-(4-Acrylamidobutoxy)-5-hydroxy-p-benzoquinone;
2,5-Bis(4-acrylamidobutoxy)-p-benzoquinone;
3-(4-Acrylamidobutoxy)-2-hydroxybenzaldehyde;
2,4-Bis(4-acrylamidobutoxy)benzaldehyde;
4-(4-Acrylamidobutoxy)-2-hydroxyacetophenone;
2,4-Bis(4-acrylamidobutoxy)acetophenone;
4-(4-Acrylamidobutoxy)-3-hydroxypropiophenone;
3,4-Bis(4-acrylamidobutoxy)propiophenone;
2-(4-Acrylamidobutoxy)-2'-hydroxybenzophenone;
2,2-Bis(4-acrylamidobutoxy)benzophenone;
1-(4-Acrylamidobutoxy)-4-hydroxyanthraquinone;
1,5-Bis(4-acrylamidobutoxy)anthraquinone;
2-(4-Acrylamidobutoxy)-2'-hydroxy-4-methoxybenzophenone;
2,2'-Bis(4-acrylamidobutoxy)-4-methoxybenzophenone;
4-[(4-(4-Acrylamidobutoxy)phenyl)-(4-hydroxyphenyl)methylene]-2,5-cyclohexadien-1-one;
4-[Bis(4-(4-acrylamidobutoxy)phenyl)methylene]-2,5-cyclohexadien-1-one;
2-(4-Acrylamidobutoxy)-4,6-dihydroxypropiophenone;
2,4-Bis(4-acrylamidobutoxy)-6-hydroxypropiophenone;
2,4,6-Tris(4-acrylamidobutoxy)propiophenone;
4-(4-Acrylamidobutoxy)-2',4'-dihydroxybenzophenone;
2,4,4'-Tris(4-acrylamidobutoxy)benzophenone;
2-(4-Acrylamidobutoxy)-1,4-dihydroxyanthraquinone;
2,4-Bis(4-acrylamidobutoxy)-1-hydroxyanthraquinone;
1,2,4-Tris(4-acrylamidobutoxy)anthraquinone;
2,5-Bis(4-acrylamidobutoxy)dihydroxybenzoquinone;
Tris(4-acrylamidobutoxy)hydroxybenzoquinone;
Tetrakis(4-acrylamidobutoxy)benzoquinone;
Bis(4-acrylamidobutoxy)dihydroxy-5H-benzocyclohepten-5-one;
2,3,4,6-Tetrakis(4-acrylamidobutoxy)-5H-benzocyclohepten-5-one;
2-(4-Acrylamidobutoxy)-2',4,4'-trihydroxybenzophenone;
2,4'-Bis(4-acrylamidobutoxy)-2',4-dihydroxybenzophenone;
2,2',4,4'-Tetrakis(4-acrylamidobutoxy)benzophenone;
Bis(4-acrylamidobutoxy)dihydroxyanthraquinone;
1,2,5,8-Tetrakis(4-acrylamidobutoxy)anthraquinone;
2,5-Bis(4-acrylamidobutoxy)-3,6-dichloro-1,4-benzoquinone;
2,5-Bis(4-acrylamidobutoxy)-3,6-dibromo-1,4-benzoquinone;
2,5-Bis(4-acrylamidobutoxy)-3,6-dinitro-1,4-benzoquinone;
4-Acrylamidobutyl 2-(4-acrylamidobutoxy)-3-hydroxybenzoate;
4-Acrylamidobutyl 2,3-bis(4-acrylamidobutoxy)benzoate;
Methyl 2,6-bis(4-acrylamidobutoxy)benzoate;
Sodium 3,5-bis(4-acrylamidobutoxy)benzoate;
4-Acrylamidobutyl 2,5-hydroxyphenylacetate;
Sodium 3,4-bis(4-acrylamidobutoxy)phenylacetate;
Sodium α,4-bis(4-acrylamidobutoxy)phenylacetate;
4-Acrylamidobutyl 3,4-bis(4-acrylamidobutoxy)cinnamate;
Sodium 3,4-bis(4-acrylamidobutoxy)cinnamate;
Ethylene glycol mono[2-(4-acrylamidobutoxy)benzoate;
[2-(2-(4-acrylamidobutoxy)ethoxy)ethyl]2-(4-acrylamidobutoxy)benzoate;
Sodium 4-(4-acrylamidobutoxy)phenyllactate;
4-Acrylamidobutyl 4-(4-acrylamidobutoxy)-3-methoxymandelate;
Sodium α,4-bis(4-acrylamidobutoxy)-3-methoxyphenylacetate;
Sodium 4-(4-acrylamidobutoxy)-3-methoxyphenyllactate;
Sodium 2-(4-acrylamidobutoxy)-3-[4-(4-acrylamidobutoxy)-3-methoxyphenyl]propionate;
Di(4-acrlamidobutyl)2,2'-bis(4-acrylamidobutoxy)-5,5'-methylenebisbenzoate;
4-Acrylamidobutyl 2-[bis(4-(4-acrylamidobutoxy)phenyl)methyl]benzoate;
Sodium 2-(4-acrylamidobutoxy)-3-[4-(4-acrylamidobutoxy)phenyl]propionate;
Di(4-acrylamidobutyl) 1,1'-methylenebis[2-(4-acrylamidobutoxy)naphthalene-3-carboxylate];
Sodium 4,4-bis[4-(4-acrylamidobutoxy)phenyl]butyrate;
4-Acrylamidobutyl 3,4,5-tris(4-acrylamidobutoxy)benzoate;
Sodium 3,4,5-tris(4-acrylamidobutoxy)benzoate;
Ethyl 3,4,5-tris(4-acrylamidobutoxy)benzoate;
Isobutyl 3,4,5-tris(4-acrylamidobutoxy)benzoate;
Lauryl 3,4,5-tris(4-acrylamidobutoxy)benzoate;
Stearyl 3,4,5-tris(4-acrylamidobutoxy)benzoate;
4-acrylamidobutyl 2,4,6-tris(4-acrylamidobutoxy)benzoate;
Sodium α,3,4-tris(4-acrylamidobutoxyphenyl)acetate;
1,2-Bis(4-acrylamidobutoxy)-4-chloroacetylbenzene;
N-[2,5-bis(4-acrylamidobutoxy)benzoyl]glycine sodium; and etc.

As substituted derivatives of those obtained by substituting mercapto groups and/or sulfo groups or their salts to aromatic rings of the above-described compounds and those formed by bonding such groups to the aromatic rings via thio groups, may for example be mentioned:

Disodium 2-(4-acrylamidobutoxy)-1-hydroxy-3,5-benzenedisulfonate;
Disodium 1,2-bis(4-acrylamidobutoxy)-3,5-benzenedisulfonate;
2-(4-Acrylamidobutoxy)-6-hydroxymethyl-4-methylthiotoluene;
2-(4-Acrylamidobutoxy)-6-(4-acrylamidobutoxymethyl)-4-methylthiotoluene;
Sodium 2-(4-acrylamidobutoxy)-3-hydroxy-6-naphthalenesulfonate;
Sodium 2,3-bis(4-acrylamidobutoxy-6-naphthalenesulfonate;
Disodium 1,8-bis(4-acrylamidobutoxy)-3,6-naphthalenedisulfonate;
Sodium 4-[4-(4-acrylamidobutoxy)-2-hydroxyphenylazo]benzenesulfonate;
1,1-Thiobis[4-(4-acrylamidobutoxy)benzene];
Bis[4-(4-acrylamidobutoxy)phenyl]sulfon;
Sodium 1,2-bis(4-acrylamidobutoxy)anthraquinone-3-sulfonate;
Di(4-acrylamidobutyl) 5,5'-thiobis[2-(4-acrylamidobutoxy)benzoate];

Sodium 4-[2-(4-acrylamidobutoxy)-5-methylphenylazo]-3-hydroxy-1-naphthalenesulfonate;
Sodium 3-(4-acrylamidobutoxy)-4-[2-(4-acrylamidobutoxy)-5-methylphenylazo]-1-naphthalenesulfonate;
2-(4-Acrylamidobutoxy)-2'-hydroxy-6,6'-dinaphthyldisulfide;
2,2'-Bis(4-acrylamidobutoxy)-6,6'-dinaphthyldisulfide;
4,4'-Thiobis[5-(4-acrylamidobutoxy)-2-tert-butyltoluene]; etc.

Exemplary substituted derivatives of compounds which contain OH-substituted heterocyclic rings may, include:

N-[4-(5-formylfurfuryloxy)butyl]acrylic amide;
3-(4-Acrylamidobutoxy)-2-methyl-4-pyrone;
4-(4-Acrylamidobutoxy)-2,5-dimethyl-3(2H)-furanone;
4-(4-Acrylamidobutoxy)-4-methyl-oxan-2-one;
4-(4-Acrylamidobutoxy)-4,4-dimethyl-oxolan-2-one;
3-(4-Acrylamidobutoxy)-2-ethyl-4-pyrone;
4-(4-Acrylamidobutoxy)coumarin;
7-(4-Acrylamidobutoxy)coumarin;
7-(4-Acrylamidobutoxy)-4-methylcoumarin;
3-(4-Acrylamidobutoxy)flavone;
2-Methyl-3-(4-acrylamidobutoxy)-4H-pyran-4-one;
N-[4-(Tetrahydrofurfuryloxy)butyl]acrylic amide;
N-[4-(5-Methylfurfuryloxy)butyl]acrylic amide;
2-(4-Acrylamidobutoxymethyl)tetrahydrofuran;
N-(4-Furfuryloxybutyl)acrylic amide;
4-(4-Acrylamidobutoxymethyl)-2,2-dimethyl-1,3-dioxolan;
5-(4-Acrylamidobutoxy)-1,3-benzodioxol;
9-(4-Acrylamidobutoxy)xanthene;
N-[2-(4-Acrylamidobutoxy)ethyl]ethyleneimine;
2-(4-Acrylamidobutoxy)pyrimidine;
4-(4-Acrylamidobutoxy)methylimidazole;
2-(4-Acrylamidobutoxy)methyl-1-methyl-5-nitroimidazole;
3-(4-Acrylamidobutoxy)pyridine;
3-(4-Acrylamidobutoxy)piperidine;
2-(4-Acrylamidobutoxymethyl)pyridine;
5-[2-(4-Acrylamidobutoxy)ethyl]-4-methylthiazole;
1-(4-Acrylamidobutoxymethyl)-5,5-dimethylhydantoin;
4-(4-Acrylamidobutoxymethyl)-2,4-dimethyloxazoline;
1-[2-(4-Acrylamidobutoxy)ethyl]-2-pyrrolidone;
1-[2-(4-Acrylamidobutoxy)ethyl]pyrrolidine;
1-[2-(4-Acrylamidobutoxy)ethyl]morpholine;
1-[2-(4-Acrylamidobutoxy)ethyl]piperazine;
2-[2-(4-Acrylamidobutoxy)ethyl]pyridine;
3-(4-Acrylamidobutoxy)quinoclidine;
N-[3-(4-Acrylamidobutoxy)propyl]-2-pyrrolidone;
1-[2-(4-Acrylamidobutoxy)ethyl]piperidine;
N-[2-(4-Acrylamidobutoxy)propyl]morpholine;
5-(4-Acrylamidobutoxy)indole;
N-[2-(4-Acrylamidobutoxy)ethyl]hexamethyleneimine;
4-[3-(4-Acrylamidobutoxy)propyl]pyridine;
8-(4-Acrylamidobutoxy)-5,7-dichloroquinoline;
8-(4-Acrylamidobutoxy)-5,7-dibromoquinoline;
8-(4-Acrylamidobutoxy)-5-fluoroquinoline;
8-(4-Acrylamidobutoxy)-5-chloroquinoline;
8-(4-Acrylamidobutoxy)quinoline;
4-(4-Acrylamidobutoxy)-2,2,6,6-tetramethylpiperidine;
8-(4-Acrylamidobutoxy)-2-methylquinoline;
3-[2-(4-acrylamidobutoxy)ethyl]indole;
7-(4-Acrylamidobutoxy)phenoxazin-3-one;
1-(4-Acrylamidobutoxy)phenazine;
8-(4-Acrylamidobutoxy)-7-(n-propyl)quinoline;
Sodium 3-(4-acrylamidobutoxy)flavone-2-sulfonate;
4-(4-Acrylamidobutoxy)-1-methyl-2-quinoline;
Sodium 3-(4-acrylamidobutoxy)-2-methylquinoline-4-carboxylate;
6-(4-Acrylamidobutoxy)-9-(3,4,5,6-tetrachloro-2-carboxyphenyl)-2,4,5,7-tetrabromo-3-isoxanthone sodium;
(4-Acrylamidobutoxymethyl)ferrocene;
6-(4-Acrylamidobutoxy)-4-(4-acrylamidobutylamino)-2-(4-acrylamidobutylthio)pyrimidine;
4-(4-Acrylamidobutoxymethyl)-1-(4-acrylamidobutyl)imidazole;
3-(4-Acrylamidobutoxy)-1-(4-acrylamidobutyl)piperidine;
4-(4-Acrylamidobutoxy)-1-(4-acrylamidobutyl)piperidine;
1-(4-Acrylamidobutoxymethyl)-3-(4-acrylamidobutyl)-5,5-dimethylhydantoin;
1-[2-(4-Acrylamidobutoxy)ethyl]-4-(4-acrylamidobutyl)piperazine;
5-(4-Acrylamidobutoxy)-1-(4-acrylamidobutyl)indole;
4-(4-Acrylamidobutoxy)-1-(4-acrylamidobutoxy)-1-acrylamidobutyl-2,2,6,6-tetramethylpiperidine;
Sodium 5-(4-acrylamidobutoxy)-1-(4-acrylamidobutyl)indole-3-acetate;
3-[2-(4-Acrylamidobutoxy)ethyl]-1-(4-acrylamidobutyl)indole;
2-(4-Acrylamidobutoxy)-3-hydroxypyridine;
2,3-Bis(4-acrylamidobutoxy)pyridine;
2-(4-Acrylamidobutoxymethyl)-5-hydroxy-4-pyrone;
5-(4-Acrylamidobutoxy)-2-(acrylamidobutoxymethyl)-4-pyrone;
Sodium 2,6-dihydoxyisonicotinate;
2-(4-Acrylamidobutoxymethy)-6-hydroxymethylpyridine;
2,6-Bis(4-acrylamidobutoxymethyl)pyridine;
2-(4-Acrylamidobutoxy)-3-hydroxyquinoxaline;
2,3-Bis(4-acrylamidobutoxy)quinoxaline;
3-(4-Acrylamidobutoxy)-2,4-dimethyl-5-hydroxymethylpyridine;
5-(4-Acrylamidobutoxymethyl)-3-hydroxy-4-hydroxymethyl-2-methylpyridine;
3-(4-Acrylamidobutoxy)-4,5-bis(hydroxymethyl)-2-methylpyridine;
3-(4-Acrylamidobutoxy)-5-(4-acrylamidobutoxymethyl)-4-hydroxymethyl-2-methylpyridine;
3-(4-Acrylamidobutoxy)-4,5-bis(4-acrylamidobutoxymethyl)-2-methylpyridine;
4-(4-Acrylamidobutoxy)-2-hydroquinoline;
2,4-Bis(4-acrylamidobutoxy)quinoline;
1,3,5-Tris[2-(4-acrylamidobutoxy)ethyl]-1,3,5-triazin-2,4,6-trione;
6-(4-Acrylamidobutoxy)-7-hydroxy-4-methylcoumarin;
6,7-Bis(4-acrylamidobutoxy)-4-methylcoumarin;
4-[3-(4-Acrylamidobutoxy)propyl]-N-(2-hydroxyethyl)piperidine;
7-(4-Acrylamidobutoxy)-5-hydroxy-3,4'-dimethoxyflavone;
1,3-Bis[N-(2-(4-acrylamidobutoxy)ethyl)-4-piperidyl]propane;
3,3-Bis[4-(4-acrylamidobutoxy)-3-methylphenyl]-(1(3H)-isobenzofuranone;
4-(4-Acrylamidobutoxy)-2-alkylcarbonyloxymethyl-3,5-dihydroxyoxane;
2-Acetoxymethyl-3,5-bis(4-acrylamidobutoxy)-4-hydroxyoxane;
2-Acetoxymethyl-3,4,5-tris(4-acrylamidobutoxy)oxane;
N-[2-(4-Acrylamidobutoxy)ethyl]-4-[3-(4-acrylamidobutoxypropyl]piperidine; etc.

Certain compounds of this invention will next be described by way of example by setting $R_1$ at a benzene ring, $\beta$ at 1, and $\alpha, \alpha', \beta', 1, 1'$ and $q$ at 0 while changing $R_2$ to a hydrogen atom or methyl group and m to 4–20 in the general formula (I).

Illustrative of such compounds may include:
N-(4-Phenoxybutyl)acrylic amide;
N-(4-Phenoxybutyl)methacrylic amide;
N-(5-Phenoxypentyl)acrylic amide;
N-(5-phenoxypentyl)methacrylic amide;
N-(6-Phenoxyhexyl)acrylic amide;
N-(6-Phenoxyhexyl)methacrylic amide;
N-(8-Phenoxyoctyl)acrylic amide;
N-(8-Phenoxyoctyl)methacrylic amide;
N-(10-Phenoxydecyl)acrylic amide;
N-(10-Phenoxydecyl)methacrylic amide;
N-(12-Phenoxydodecyl)acrylic amide;
N-(12-Phenoxydodecyl)methacrylic amide;
N-(14-Phenoxytetradecyl)acrylic amide;
N-(14-Phenoxytetradecyl)methacrylic amide;
N-(16-Phenoxyhexadecyl)acrylic amide;
N-(16-Phenoxyhexadecyl)methacrylic amide;
N-(18-Phenoxyoctadecyl)acrylic amide;
N-(18-Phenoxyoctadecyl)methacrylic amide;
N-(20-Phenoxyeicosyl)acrylic amide;
N-(20-Phenoxyeicosyl)methacrylic amide; etc.

The above-exemplified unsaturated cyclic amido-substituted ether compounds may be prepared by reacting the cyclic halogen-substituted ether compounds represented by the general formula (II) with the unsaturated amide compounds represented by the general formula (III) in the presence of a strong basic substance in an aprotic polar solvent.

The structures of the halogen-substituted cyclic ether compounds and unsaturated amide compounds, both of which are useful in the practice of this invention, are exactly the same as the general formula described in detail in connection with the unsaturated cyclic amide-substituted ether compounds and are thus not described in detail here. In the case of the cyclic halogen-substituted ether compounds, are included those obtained by substituting at least one hydroxyl groups of compounds, which contain OH-substituted carbocyclic rings, with halogen-substituted ether groups and those obtained by substituting at least one hydroxyl groups of compounds, which contain OH-substituted heterocyclic rings, with halogen-substituted ether groups.

Where A stands for a haloalkyl group in the general formula (II), the above-mentioned alkyl group contains one or more halogen atoms substituted thereto. If two or more halogen atoms are contained, they may be different halogen atoms.

Unsaturated amide compounds are included acrylic amide and methacrylic amide.

As a specific method for conducting the reaction in the presence of the strong basic substance in the present invention, there are two methods, one being to dissolve the strong basic substance in the liquid reaction mixture and then to initiate the reaction and the other to initiate the reaction with the strong basic substance being in a suspended state. Although both methods may be applicable in the present invention, it has surprisingly been found that an initiation of the reaction in the presence of the strong basic substance in a suspended state is preferred from the viewpoint of the reaction efficiency such as suppression to side reactions. As a more specific method for initiating the reaction in the presence of the strong basic substance in such a suspended state, it may be feasible to employ any suitable method, for example, to charge all the three reaction materials into the aprotic polar solvent and then to mix them there to suspend the strong basic substance therein; to suspend the strong basic substance in the aprotic polar solvent and then to charge the cyclic halogen-substituted ether compounds and unsaturated amide compound simultaneously to the resulting suspension for their reaction; or to either dissolve or suspend the cyclic halogen-substituted ether compounds and unsaturated amide compounds in the aprotic polar solvent and thereafter to add and suspend the strong basic substance.

Any aprotic polar solvent may be employed as a reaction solvent in the present invention. As exemplary aprotic polar solvents, may be mentioned acetonitrile, N,N-dimethylformamide, N,N-dimethylacetamide, dimethylsulfoxide, sulforan, tetraglime, dioxane, N-methylpyrrolidone, and so on.

In a reaction system in which the process of this invention is effected, it is preferred to initiate the reaction in such a state that at least part of the strong basic substance is suspended. The amount of water in such a state is generally 6 wt. % or so as the water quantity in the reaction system. If the amount of water should exceed this level, side reactions such as hydrolysis of the dihalogen-substituted compound tend to occur and the yield will be lowered significantly. In order to allow the reaction to proceed efficiently and hence to increase the yield of the intended product, it is preferred to control the water content of the reaction system below 5 wt. %.

No particular limitation is imposed on the amount of a solvent to be used. The solvent may amount to 5–95 wt. % or preferably 10–90 wt. % of the total weight of reaction materials which include the solvent.

On the other hand, the strong basic substance to be employed in the present invention is a solid substance. Any strong basic substances may be used so long as when either dissolved or suspended in water, the pHs of resulting aqueous solutions are above 10 or preferably above 11. As such basic substances, may for example be mentioned alkali metal hydroxides, alkali metal oxides, alkali metal carbonates, alkaline earth metal hydroxides, alkaline earth metal oxides, alkali metal hydrides, alkaline earth metal hydrides, alkali metal amides, alkali metal alkoxides, etc.

The following specific substances may be given by way of example as the above-described substances. Illustrative of alkali metal hydroxides include sodium hydroxide, potassium hydroxide, lithium hydroxide, rubidium hydroxide and cesium hydroxide. As alkali metal oxides, may for example be mentioned sodium oxide, potassium oxide, lithium oxide, rubidium oxide and cesium oxide. Exemplary alkali metal carbonates may include sodium carbonate, potassium carbonate, lithium carbonate, rubidium carbonate and cesium carbonate. Illustrative of alkaline earth metal hydroxides may include beryllium hydroxide, magnesium hydroxide, calcium hydroxide, strontium hydroxide and barium hydroxide. As alkaline earth metal oxides, may for example be mentioned beryllium oxide, magnesium oxide, calcium oxide, strontium oxide and barium oxide. Exemplary alkali metal hydrides may include sodium hydride, potassium hydride and lithium hydride. As exemplary alkaline earth metal hydrides, may be mentioned beryllium hydride, magnesium hydride and calcium hydride. Alkali metal amides are compounds obtained by substituting ammonia with alkali metals, including for example sodium amide, potassium amide and lithium amide. Alkali metal alkoxides are compounds obtained by substituting the protons of the hydroxyl groups of alcohols with alkali metals, including for example, sodium methoxide, sodium ethoxide, sodium t-butoxide, potassium methoxide, potassium ethoxide, potassium t-butoxide.

Among the above-described basic substances, those suitable in the practice of the process of this invention may for example be alkali metal hydroxides, alkaline earth metal hydroxides, alkali metal oxides, alkaline earth metal oxides, alkali metal carbonates and the like.

Each of these strong basic substances is usually provided in a solid form for the reaction. The reaction is initiated in such a state that at least part of the strong basic substance is suspended in the liquid reaction mixture.

In the practice of the present invention, the relative amounts of the raw materials, i.e., the cyclic halogen-substituted ether compound, unsaturated amide compound and strong basic substance to be used vary depending on the reactivity between the cyclic halogen-substituted ether compound and the unsaturated amide compounds, etc. and cannot thus be specified as any constant amounts or amount ranges.

However, the cyclic halogen-substituted ether compound may generally be used in a molar amount 0.2–20 times or preferably 0.3–10 times the unsaturated amide compound. On the other hand, the strong basic substance may approximately be used in a molar amount 0.2–15 times or preferably 0.5–10 times the amide compound.

A polymerization inhibitor may also be added in order to avoid polymerization of raw materials and reaction product during the reaction and purification steps. Although no particular limitation is vested on the polymerization inhibitor, use of a phenol-type inhibitor, amine-type inhibitor, mercaptan-type inhibitor or copper powder may generally be mentioned.

As a reaction method, an ordinary reaction vessel may be employed. When using a strong basic substance having a low solubility, the reaction may be effected in accordance with the flow method, namely, by packing the strong basic substance in a column and then causing a mixed solution of the cyclic halogen-substituted ether compound and unsaturated amide compound to recirculate through the column. Use of a reaction vessel is however more convenient for the maintenance of the reaction apparatus.

The reaction temperature is dependent on the reactivity between each cyclic halogen-substituted ether compound and unsaturated amide compound to be employed. A lower reaction temperature will result in a reduction to the progress of the reaction. On the other hand, a higher reaction temperature will induce side reactions such as hydrolysis of the unsaturated amide compound and will hence result in a reduction to the yield of the intended product. Therefore, the reaction is generally carried out within a temperature range of $-30°-+100°$ C. or preferably $-20°-+70°$ C. So long as the reaction is carried out within this temperature range, it may not be absolutely necessary to maintain the temperature at a constant level during the reaction. It may be possible to change the reaction temperature suitably to allow the reaction to proceed efficiently while precisely observing the progress of the reaction.

Similar to the reaction temperature, the reaction time varies depending on each cyclic halogen-substituted ether compound and unsaturated amide compound to be used. The reaction time is however within 30 hours at the longest, and normally within 20 hours. The progress of the reaction can be observed by depending on changes in nature or state of the reaction system or by determining the concentrations of the raw materials and intended product in the liquid reaction mixture with gas chromatography or high-speed liquid chromatography.

After the reaction, the intended product of high purity can be obtained by filtering off the by-produced metal halide and distilling the resulting filtrate under reduced pressure. Where the metal halide is dissolved in the liquid reaction mixture, the intended product of high purity can be obtained by driving off the solvent, removing the metal halide with a combination of solvents capable of forming two layers such as hexane-water, benzene-water or chloroform-water, and then distilling the residue under reduced pressure. However, the compounds of this invention generally have high boiling points and many of these compounds have non-volatile properties. In addition, they contain readily-polymerizable double bonds in their molecules. Therefore, they may not be purified by distillation in many instances. Even in such cases, the intended products may still be isolated with good purity by solvent extraction or recrystallization or by using an adsorbent such as silLca gel, alumina, activated carbon, ion-exchange resin, adsorptive resin or the like. Furthermore, two or more of the above-mentioned purification methods may be used in combination.

Where the reaction solvent has great miscibility with water like dimethylsulfoxide or N,N-dimethylformamide and the intended product is highly hydrophobic, it is feasible to isolate the intended product after the reaction, for example, by adding an aliphatic hydrocarbon solvent such as hexane to the liquid reaction mixture to extract the intended product, adding water to the liquid reaction mixture to separate the intended product as an oil layer, or extracting and separating the intended product with a solvent capable of forming two layers when mixed with water, such as benzene, toluene or chloroform.

According to the present invention, a variety of cyclic unsaturated amido-substituted ether compounds can be prepared using the same reaction procedure and the same reaction reactor. Therefore, the present invention is suitable for the preparation of various products in small volumes.

The cyclic unsaturated amido-substituted ether compounds of this invention have been obtained by introducing an extremely wide variety of substituent groups in side chains as shown by the above-exemplified compounds. They can be used for various applications depending on the nature of introduced substituent groups. As specific utility, may be mentioned principal raw materials, auxiliary raw materials, crosslinking agents and the like for adhesives, paints, paper-converting or paper-conditioning agents, textile-processing agents, emulsions, urethane-hardening agents, pigments, dispersants, additives to plastics, high-molecular coagulants, ion-exchange resins, adsorption and separation resins, chelate resins, optical lenses, photosensitive resins, soft contact lenses, hygroscopic resins, binders for magnetic materials, binders for composite materials, high-molecular catalysts, clinical reagents, biocompatible materials, enzyme-immobilizing base materials, etc. Namely, the compounds of this invention can be used in a variety of fields.

This invention will next be described further by the following Examples.

EXAMPLE 1

Added to 20 ml of N,N-dimethylformamide were 1.34 g of acrylic amide and 3.4 g of (4-bromobutoxy)-benzene. With stirring, 0.88 g of flaky potassium hydroxide which had been ground in a mortar was added. Phenothiazine was added in an amount of 0.5% based on the acrylic amide. After they were reacted at 0°–5° C. for 6 hours, insoluble matter was filtered off from the liquid reaction mixture. The solvent and unreacted raw materials were distilled off from the filtrate. The residue was extracted with benzene-water, thereby obtaining the intended product in the benzene layer. Benzene was then driven off from the benzene layer to obtain 2.66 g of N-(4-phenoxybutyl)acrylic amide (yield: 81%). It was purified further with column chromatography in which silica gel and benzene were used as an adsorbent and developer respectively. Its melting point was measured and its elementary analysis was also conducted. The following results were obtained. Melting point: 46°–47° C. Elementary analysis data: C, 71.29% (Calculated: 71.19%); H, 7.31% (7.82%); N, 6.15% (6.38%).

EXAMPLES 2–12

Reactions were carried out under the conditions shown in Tables 1 and 2, using the combinations of raw materials, strong basic substances and solvents given in Table 1. After the reactions, the respective reaction mixtures were treated in exactly the same manner as in Example 1. Results are shown in Table 2.

TABLE 1

| Ex. | Amide Compound (g) | Halogen-Substituted Ether Compound (g) | Strong Basic Substance (g) | Solvent (ml) | Reaction Temp. (°C.) / Reaction Time (hr.) |
|---|---|---|---|---|---|
| 2 | Acrylic amide 0.70 | 2-(4-Bromobutoxy)-anthraquinone 3.0 | KOH 0.44 | DMF 20 | 0 – 5 / 6 |
| 3 | Acrylic amide 0.54 | 4-(4-Bromobutoxy)-benzophenone 2.0 | KOH 0.54 | DMF 20 | 0 – 5 / 6 |
| 4 | Acylic amide 0.58 | 1-(4-Bromobutoxy-2-tert-butyl-4-methoxybenzene 2.0 | KOH 0.36 | DMF 20 | 0 – 5 / 6 |
| 5 | Acrylic amide 0.40 | 1-(4-Bromobutoxy-2,4,6-tribromo-benzene 2.0 | KOH 0.25 | DMF 20 | 15 – 20 / 6 |
| 6 | Acrylic amide 0.66 | 3-(4-Bromobutoxy)-N,N—diethylaniline 2.0 | KOH 0.42 | DMF 20 | 0 – 5 / 6 |
| 7 | Acrylic amide 0.70 | 1-(4-Bromobutoxy)-4-methoxybenzene 2.0 | KOH 0.44 | DMF 20 | 0 – 5 / 6 |
| 8 | Acrylic amide 0.66 | 1-(4-Bromobutoxy)-4-nitrobenzene 2.0 | KOH 0.42 | DMF 20 | 0 – 5 / 6 |
| 9 | Acrylic amide 0.62 | 1-(4-Bromobutoxy)-2-methoxy-4-(1-propenyl)benzene 2.0 | KOH 0.38 | DMF 20 | 0 – 5 / 6 |
| 10 | Acrylic amide 0.60 | 1-(4-Bromobutoxy)-4-phenylbenzene 2.0 | KOH 0.38 | DMF 20 | 0 – 5 / 6 |
| 11 | Acrylic amide 0.64 | 2-(4-Bromobutoxy)-naphthalene 2.0 | KOH 0.42 | DMAC 20 | 15 – 20 / 6 |
| 12 | Acrylic amide 0.90 | 2,2-Bis(3,5-dibromo-4-bromobutoxyphenyl)-propane 4.0 | KON 0.58 | DMF 20 | 0 – 5 / 6 |

Note: DMF: N,N—Dimethylformamide; DMAC: N,N—Dimethylacetamide

TABLE 2

| Ex. | Reaction Product | m.p. (°C.) | C | H | N | Yield g, (%) |
|---|---|---|---|---|---|---|
| 2 | 2-(4-Acrylamidobutoxy)-anthraquinone | 116–117 | 71.98 (72.18) | 5.99 (5.49) | 4.14 (4.00) | 2.42 (83) |
| 3 | 2-(4-Acrylamidobutoxy)-benzophenone | 70–71 | 74.56 (74.26) | 6.75 (6.55) | 4.86 (4.33) | 1.54 (79) |
| 4 | N—(4-(2-tert-Butyl-4-methoxyphenyl)butyl) acrylic amide | 104–105 | 70.24 (70.77) | 8.49 (8.92) | 4.70 (4.58) | 1.22 (63) |
| 5 | N—(4-(2,4,6-Tribromo-phenoxy)butylacrylic amide | 74–75 | 34.80 (34.23) | 3.39 (3.10) | 2.99 (3.07) | 1.43 (73) |
| 6 | N—(4-(3-(Diethylamino)-phenoxy)butyl)acrylic amide | 57–58 | 70.17 (70.29) | 9.33 (9.04) | 9.98 (9.64) | 1.30 (67) |
| 7 | N—(4-(4-Methoxyphenoxy)-butyl)acrylic amide | 79–80 | 67.31 (67.43) | 7.77 (7.69) | 5.33 (5.61) | 1.41 (73) |
| 8 | N—(4-(4-Nitrophenoxy) butyl)acrylic amide | 58–59 | 58.45 (59.07) | 6.02 (6.11) | 10.22 (10.60) | 1.52 (79) |

TABLE 2-continued

| Ex. | Reaction Product | m.p. (°C.) | Elementary Analysis Data (%) (Calculated) | | | Yield g, (%) |
|---|---|---|---|---|---|---|
| | | | C | H | N | |
| 9 | N—(4-(2-Methoxy-4-(1-propenyl)phenoxybutyl-acrylic amide | 78–79 | 70.78 (70.54) | 7.80 (8.02) | 4.99 (4.84) | 1.22 (63) |
| 10 | N—(4-(4-Phenylphenoxy)-butyl)acrylic amide | 127–128 | 77.58 (77.24) | 7.66 (7.17) | 4.69 (4.74) | 1.61 (83) |
| 11 | 2-(4-Acrylamidobutoxy)-naphthalene | 85–86 | 75.81 (75.79) | 6.90 (7.12) | 5.45 (5.20) | 1.65 (85) |
| 12 | 2,2-Bis(4-(4-acrylamido-butoxy)-3,5-dibromo-phenyl)propane | 108–109 | 43.60 (43.20) | 5.98 (5.71) | 3.88 (3.48) | 2.99 (75) |

EXAMPLE 13

Added to 20 ml of N,N-dimethylformamide were 1.96 g of acrylic amide and 4.0 g of 2,2-bis(4-bromobutoxyphenyl)propane. With stirring, 0.96 g of flaky potassium hydroxide which had been ground in a mortar was added. Phenothiazine was added in an amount of 0.5% based on the acrylic amide. After they were reacted at 0°–5° C. for 6 hours, insoluble matter was filtered off from the liquid reaction mixture. The solvent and unreacted raw materials were distilled off from the filtrate. The residue was extracted with benzene-water, thereby obtaining the intended product in the benzene layer. Benzene was then driven off from the benzene layer to obtain 3.01 g of 2,2-bis[4-(4-acrylamidobutoxy)phenyl]propane (yield: 77%). It was purified further with column chromatography in which silica gel and a mixed benzene-methanol solvent were used as an adsorbent and developer respectively. Its refractive index at 25° C. was measured and its elementary analysis was also conducted. The following results were obtained. Refractive index (25° C.): 1.5622. Elementary analysis data: C, 72.97% (Calculated: 72.75%); H, 8.58% (8.01%); N, 5.67% (5.85%).

EXAMPLES 14–30

Reactions were carried out under the conditions shown in Table 3, using the combinations of raw materials, strong basic substances and solvents given in Table 3. After the reactions, the respective reaction mixtures were treated in exactly the same manner as in Example 13. Results are shown in Table 4.

TABLE 3

| Ex. | Amide Compound (g) | Halogen-Substituted Ether Compound (g) | Strong Basic Substance (g) | Solvent (ml) | Reaction Temp. (°C.) / Reaction Time (hr.) |
|---|---|---|---|---|---|
| 14 | Acrylic amide 1.06 | 2-(4-Bromobutoxy)-ethyl)benzene 3.0 | KOH 0.68 | DMF 20 | 0 – 5 / 6 |
| 15 | Acrylic amide 0.64 | N—(2-(4-Bromobutoxy)-ethyl)-N—ethylaniline 2.4 | KOH 0.40 | DMF 20 | 0 – 5 / 6 |
| 16 | Acrylic amide 0.80 | (4-Bromobutoxy)-cyclohexane 2.0 | KOH 0.50 | DMF 20 | 0 – 5 / 6 |
| 17 | Acrylic amide 0.66 | (4-Bromobutoxy)-dicyclopentadiene 2.0 | KOH 0.42 | DMF 20 | 0 – 5 / 6 |
| 18 | Acrylic amide 0.80 | 1-Bromo-4-furfuryl-oxybutane 2.0 | KOH 0.50 | DMF 20 | 0 – 5 / 6 |
| 19 | Acrylic amide 1.00 | 2-(4-Bromobutoxy-methyl)tetrahydro-pyrane 2.7 | KOH 0.64 | DMF 20 | 0 – 5 / 6 |
| 20 | Acrylic amide 0.96 | 2-Methyl-3-(4-bromo-butoxy)-4H—pyran-4-one 2.7 | KOH 0.62 | DMF 20 | 0 – 5 / 6 |
| 21 | Acrylic amide 0.78 | 1-(4-Bromobutoxy)-4-nonylbenzene 3.0 | KOH 0.50 | DMF 20 | 0 – 5 / 6 |
| 22 | Acrylic amide 0.76 | (4-Bromobutoxy-methyl)benzene 2.0 | KOH 0.48 | DMF 20 | 0 – 5 / 6 |
| 23 | Acrylic amide 0.90 | 1-(4-Bromobutoxy)-2-(4-bromobutoxy-carbonyl)benzene 2.0 | KOH 0.58 | DMF 20 | 0 – 5 / 6 |
| 24 | Acrylic amide 0.94 | 2,6-Bis(4-bromo-butoxy)toluene 2.0 | KOH 0.60 | DMF 20 | 0 – 5 / 6 |
| 25 | Acrylic amide 1.00 | (2-(4-Bromobutoxy)-ethoxy)benzene 2.0 | KOH 0.64 | DMF 20 | 0 – 5 / 6 |
| 26 | Acrylic amide 0.72 | 4-(4-Bromobutoxy)-benzaldehyde 2.0 | KOH 0.44 | DMF 20 | 0 – 5 / 6 |

TABLE 3-continued

| Ex. | Amide Compound (g) | Halogen-Substituted Ether Compound (g) | Strong Basic Substance (g) | Solvent (ml) | Reaction Temp. (°C.) / Reaction Time (hr.) |
|---|---|---|---|---|---|
| 27 | Acrylic amide 1.04 | 1,4-Bis(4-bromo-butoxy)-2-butene 2.0 | KOH 0.66 | DMF 20 | 0 – 5 / 6 |
| 28 | Acrylic amide 0.68 | (1-(4-Bromobutoxy)-2-propenyl)benzene 2.0 | KOH 0.42 | DMF 20 | 0 – 5 / 6 |
| 29 | Acrylic amide 0.70 | N—(2-(4-Bromobutoxy)-ethyl)morpholine 2.0 | KOH 0.40 | DMF 20 | 0 – 5 / 6 |
| 30 | Methacylic amide 0.88 | 2,2-Bis(4-bromobutoxy-phenyl)propane 2.0 | KOH 0.66 | DMF 20 | 0 – 5 / 6 |

TABLE 4

| Ex. | Reaction Product | Refractive index (25° C.) | Elementary Analysis Data (%) (Calculated) C | H | N | Yield g, (%) |
|---|---|---|---|---|---|---|
| 14 | N—[4-(2-phenylethoxy)-butyl]acrylic amide | 1.5248 | 72.73 (72.82) | 8.70 (8.57) | 5.52 (5.66) | 2.34 (81) |
| 15 | N—[4-(2-(N—Ethylanilino)-ethoxy)butyl]acrylic amide | 1.5441 | 69.98 (70.05) | 9.16 (9.35) | 3.48 (3.61) | 1.42 (67) |
| 16 | N—(4-cyclohexyloxy-butyl)acrylic amide | 1.4748 | 69.14 (69.27) | 10.48 (10.30) | 5.96 (6.21) | 1.28 (67) |
| 17 | N—(4-Dicyclopentadienyl-oxybutyl)acrylic amide | 1.5208 | 73.77 (73.51) | 8.57 (8.88) | 5.14 (5.30) | 1.33 (69) |
| 18 | N—(4-Furfuryloxybutyl)-acrylic amide | 1.5037 | 64.78 (64.25) | 8.33 (8.10) | 6.65 (6.24) | 1.44 (75) |
| 19 | 2-(4-Acrylamidobutoxy-methyl)tetrahydrofuran | 1.4883 | 64.31 (67.41) | 9.91 (10.00) | 5.55 (5.78) | 1.84 (71) |
| 20 | 2-Methyl-3-(4-acrylamido-butoxy)-4H—pyran-4-one | 1.5359 | 63.29 (63.85) | 6.17 (6.52) | 5.62 (5.32) | 1.90 (73) |
| 21 | N—[4-(4-Nonylphenoxy)-butyl]acrylic amide | 1.5230 | 76.78 (76.45) | 10.53 (10.22) | 4.13 (4.05) | 2.37 (81) |
| 22 | N—(4-Benzyloxydibutyl)-acrylic amide | 1.5401 | 71.19 (72.05) | 8.71 (8.22) | 5.71 (6.00) | 1.44 (75) |
| 23 | 4-Acrylamidobutyl 2-(4-acrylamidobutoxy) benzoate | 1.5389 | 64.31 (64.91) | 7.55 (7.27) | 7.46 (7.21) | 1.16 (61) |
| 24 | 2,6-Bis(4-acrylamido-butoxy)toluene | 1.5245 | 67.11 (67.34) | 7.88 (8.09) | 7.57 (7.48) | 1.20 (63) |
| 25 | N—[4-(2-Phenoxyethoxy)-butyl]acrylic amide | 1.5285 | 68.13 (68.40) | 7.84 (8.05) | 5.19 (5.31) | 2.23 (77) |
| 26 | N—[4-(4-Formylphenoxy)-butyl]acrylic amide | 1.5640 | 67.98 (67.98) | 6.09 (6.24) | 5.54 (5.66) | 1.29 (67) |
| 27 | 1,4-Bis(4-acrylamido-butoxy)-2-butene | 1.5105 | 64.07 (63.86) | 9.14 (8.95) | 8.39 (8.27) | 1.48 (78) |
| 28 | N—[4-(3-Phenyl-2-propenyl-oxy)butyl]acrylic amide | 1.5465 | 73.84 (74.08) | 8.28 (8.17) | 5.72 (5.40) | 1.45 (75) |
| 29 | 1-[2-(4-Acrylamidobutoxy)-ethyl]morpholine | 1.5045 | 60.50 (60.89) | 9.21 (9.45) | 10.47 (10.92) | 1.50 (78) |
| 30 | 2,2-Bis[4-(4-methacyl-amidobutoxy)phenyl]propane | 1.5590 | 73.86 73.47 | 8.32 8.37 | 5.05 5.52 | 1.51 (73) |

EXAMPLE 31

Added to 20 ml of N,N-dimethylformamide were 0.62 g of acrylic amide and 2.0 g of (8-bromooctyloxy)-benzene. With stirring, 0.49 g of flaky potassium hydroxide which had been ground in a mortar was added. Phenothiazine was added in an amount of 0.5% based on the acrylic amde. After they were reacted at 0°–5° C. for 6 hours, insoluble filtered off from the liquid reaction mixture. The solvent and unreacted raw materials were distilled off from the filtrate. The residue was extracted with benzene-water, thereby obtaining the intended product in the benzene layer. Benzene was then driven off from the benzene layer to obtain 1.53 g of N-(8-phenoxyoctyl)acrylic amide (yield: 79%). It was purified further with column chromatography in which silica gel and benzene were used as an adsorbent and developer respectively. Its melting point was measured and its elementary analysis was also conducted. The following results were obtained. Melting point: 45°–47° C. Elementary analysis data: C, 74.21% (Calculated: 74.14%); H, 9.09% (9.15%); N, 5.12% (5.09%).

EXAMPLE 32

In exactly the same manner as in Example 31 except that 3.0 g of (12-bromododecyloxy)benzene was used in lieu of 2.0 g of (8-bromooctyloxy)benzene in Example 31, an reaction and its post-treatment were carried out to obtain 2.26 g of N-(12-phenoxydodecyl)acrylic amide (yield: 78%). It was purified further with column chromatography in which silica gel and benzene were used as an adsorbent and developer respectively. Its melting point was measured and its elementary analysis was also conducted. The following results were obtained. Melting point: 69°–71° C. Elementary analysis data: C, 76.03% (Calculated: 76.09%); H,10.14%(10.03%); N, 4.19% (4.23%).

EXAMPLE 33

(Application as Crossl Agent

To N-acryloylpyrrolidine containing 0.2% of 2,2-bis[4-(4-acrylamidobutoxy)phenyl]propane, was added tert-butyl peroxy-2-ethylhexanoate in an amount of 1%. The resultant mixture was allowed to stand at 40° C. for 50 hours to conduct solventless polymerization, thereby obtaining a block-like polymer. The polymer was ground into powder to obtain a product. Into a graduated cylinder containing 50 ml of distilled water, 1.0 g of the powdery product was poured. The volume of water absorbed at 25° C. in the powdery product was measured. It was 23 ml.

One gram of the thus-absorbed resin was taken and placed between two glass plates each of 30 cm in length and 5 cm in width. The glass plates were displaced relative to each other over a distance of 10 cm at a relative displacement speed of 10 cm/sec. After the displacement, the upper glass plate was removed and the state of the water-absorbed resin was observed. Practically, no trace of grinding was observed on the resin.

Another resin was also prepared in exactly the same manner as in Example 33 except that N,N'-methylenebisacrylic amide was used as a crosslinking agent in place of 2,2-bis[4-(4-acrylamidobutoxy)-phenyl]propane. The resin was caused to absorb water at 25° C. in exactly the same manner. The volume of absorbed water was measured to be 23 ml.

Similarly, the water-absorbed resin was sandwiched between glass plates. After displacing the glass plates relative to each other, the upper glass plate was removed to observe the state of the water-absorbed resin. About 40% of the resin was found to have been ground.

What is claimed is:

1. Unsaturated cyclic amido-substituted ether compound represented by the following general formula (I):

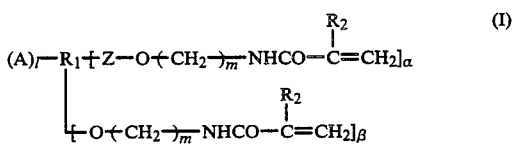

wherein: $R_1$ is an aromatic ring; Z is an alkylene group having 1 or 2 carbon atoms, an alkenylene group having 3 carbon atoms, an oxyalkylene group represented by the general formula $-(O-C_xH_{2x})-$, wherein x is an integer of 1 or 2, or an aminoalkylene group represented by the general formula:

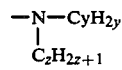

wherein y and z are each an integer of 2; A is a halogen atom, a hydroxyl group, an oxo group, a cyano group, a nitro group, a mercapto group, a sulfo group, an alkyl group having 1 to 9 carbon atoms, an alkenyl group having 3 carbon atoms, an aminoalkyl group represented by the general formula:

wherein R' and R" each are an alkyl group having 1 or 2 carbon atoms, or a group represented by the general formula RO— or RCO—, wherein R is an alkyl group having 1 carbon atom or an aryl group; $R_2$ is a hydrogen atom or a methyl group; l is an integer of 0 to 3; m is an integer of 4 to 20; α and β each stand for an integer of 0 or 1, with the proviso that $\alpha+\beta=1$.

2. The unsaturated cyclic amido-substituted ether compound as claimed in claim 1 wherein the carbocyclic aromatic ring is selected from the group consisting of benzene, naphthalene and anthracene.

3. The unsaturated cyclic amido-substituted ether compound as claimed in claim 1 wherein A is a halogen atom, an oxo group, a nitro group, an alkyl group having 1 to 9 carbon atoms, an alkenyl group having 3 carbon atoms, an aminoalkenyl group represented by the general formula:

wherein $R'_1$ and R" each are an alkyl group having 2 carbon atoms, a group represented by the general formula RO— or RCO—, wherein R is an alkyl group having 1 carbon atom or an aryl group.

4. The unsaturated cyclic amido-substituted ether compound as claimed in claim 1 wherein m stands for an integer of 4 to 12.

* * * * *